(12) United States Patent
Lozano et al.

(10) Patent No.: US 7,653,433 B2
(45) Date of Patent: *Jan. 26, 2010

(54) METHOD OF TREATING DEPRESSION, MOOD DISORDERS AND ANXIETY DISORDERS USING NEUROMODULATION

(75) Inventors: Andres M Lozano, Toronto (CA); Helen S Mayberg, Toronto (CA)

(73) Assignee: Advanced Neuromodulation Systems, Inc., Plano, TX (US)

( * ) Notice: Subject to any disclaimer, the term of this patent is extended or adjusted under 35 U.S.C. 154(b) by 301 days.

This patent is subject to a terminal disclaimer.

(21) Appl. No.: 11/469,669

(22) Filed: Sep. 1, 2006

(65) Prior Publication Data

US 2007/0005115 A1  Jan. 4, 2007

Related U.S. Application Data

(63) Continuation of application No. 10/872,277, filed on Jun. 18, 2004, now Pat. No. 7,346,395.

(60) Provisional application No. 60/511,268, filed on Oct. 15, 2003, provisional application No. 60/550,164, filed on Mar. 4, 2004.

(30) Foreign Application Priority Data

Jun. 19, 2003 (CA) .................................... 2432810

(51) Int. Cl.
*A61N 1/00* (2006.01)
(52) U.S. Cl. .......................................................... 607/3
(58) Field of Classification Search .................... 607/3, 607/45, 72; 604/890, 890.1
See application file for complete search history.

(56) References Cited

U.S. PATENT DOCUMENTS

| 3,653,385 A | 4/1972 | Burton |
| 3,731,681 A | 5/1973 | Blackshear et al. |
| 3,951,147 A | 4/1976 | Tucker et al. |
| 4,692,147 A | 9/1987 | Duggan |
| 4,772,263 A | 9/1988 | Dorman et al. |
| 4,883,057 A | 11/1989 | Broderick |
| 4,892,538 A | 1/1990 | Aebischer et al. |

(Continued)

FOREIGN PATENT DOCUMENTS

| WO | WO 0197906 | 12/2001 |
| WO | WO 03043690 | 5/2003 |
| WO | WO 03063951 | 8/2003 |

OTHER PUBLICATIONS (No Author) "Psychosurgery," The Lancet, Jul. 8, 1972, 69-70. cited by other.
Aita, "Psychosurgery: A Retrospective," Nebraska Medical J., Jul. 1991, 201-204. cited by other.

(Continued)

*Primary Examiner*—George Manuel
(74) *Attorney, Agent, or Firm*—Melissa Acosta; Peter Lando; Christopher S. L. Crawford

(57) ABSTRACT

The present application involves a method and a system for using electrical stimulation and/or chemical stimulation to treat depression. More particularly, the method comprises surgically implanting an electrical stimulation lead and/or catheter that is in communication with a predetermined site which is coupled to a signal generator and/or infusion pump that release either an electrical signal and/or a pharmaceutical resulting in stimulation of the predetermined site thereby treating the mood and/or anxiety.

28 Claims, 11 Drawing Sheets

U.S. PATENT DOCUMENTS

| | | |
|---|---|---|
| 5,119,832 A | 6/1992 | Xavier |
| 5,125,888 A | 6/1992 | Howard et al. |
| 5,263,480 A | 11/1993 | Wernicke et al. |
| 5,299,569 A | 4/1994 | Wernicke et al. |
| 5,342,410 A | 8/1994 | Braverman |
| 5,423,877 A | 6/1995 | Mackey |
| 5,458,631 A | 10/1995 | Xavier |
| 5,470,846 A | 11/1995 | Sandyk |
| 5,540,734 A | 7/1996 | Zabara |
| 5,585,118 A | 12/1996 | Stoll |
| 5,601,835 A | 2/1997 | Sabel et al. |
| 5,683,422 A | 11/1997 | Rise |
| 5,707,335 A | 1/1998 | Howard et al. |
| 5,711,316 A | 1/1998 | Elsberry et al. |
| 5,713,923 A | 2/1998 | Ward et al. |
| 5,716,377 A | 2/1998 | Rise et al. |
| 5,735,505 A | 4/1998 | Walton |
| 5,735,814 A | 4/1998 | Elsberry et al. |
| 5,750,103 A | 5/1998 | Cherksey |
| 5,752,911 A | 5/1998 | Canedo et al. |
| 5,779,694 A | 7/1998 | Howard et al. |
| 5,792,186 A | 8/1998 | Rise |
| 5,814,014 A | 9/1998 | Elsberry et al. |
| 5,832,932 A | 11/1998 | Elsberry et al. |
| 5,833,709 A | 11/1998 | Rise et al. |
| 5,840,069 A | 11/1998 | Robinson |
| 5,853,385 A | 12/1998 | Emerich et al. |
| 5,873,849 A | 2/1999 | Bernard |
| 5,921,245 A | 7/1999 | O'Donnell, Jr. |
| 5,938,688 A | 8/1999 | Schiff |
| 5,975,085 A | 11/1999 | Rise |
| 5,978,702 A | 11/1999 | Ward et al. |
| 6,015,786 A | 1/2000 | Mascarenhas et al. |
| 6,016,449 A | 1/2000 | Fischell et al. |
| 6,036,459 A | 3/2000 | Robinson |
| 6,042,579 A | 3/2000 | Elsberry et al. |
| 6,051,017 A | 4/2000 | Loeb et al. |
| 6,093,180 A | 7/2000 | Elsberry |
| 6,094,598 A | 7/2000 | Elsberry et al. |
| 6,128,537 A | 10/2000 | Rise |
| 6,129,685 A | 10/2000 | Howard, III |
| 6,132,361 A | 10/2000 | Epstein et al. |
| 6,161,045 A | 12/2000 | Fischell et al. |
| 6,176,242 B1 | 1/2001 | Rise |
| 6,216,030 B1 | 4/2001 | Howard et al. |
| 6,227,203 B1 | 5/2001 | Rise et al. |
| 6,230,049 B1 | 5/2001 | Fischell et al. |
| 6,248,126 B1 | 6/2001 | Lesser et al. |
| 6,251,115 B1 | 6/2001 | Williams et al. |
| 6,251,669 B1 | 6/2001 | Luskin |
| 6,263,237 B1 | 7/2001 | Rise |
| 6,278,895 B1 | 8/2001 | Bernard |
| 6,353,754 B1 | 3/2002 | Fischell et al. |
| 6,353,762 B1 | 3/2002 | Baudino et al. |
| 6,366,813 B1 * | 4/2002 | DiLorenzo .................. 607/45 |
| 6,399,574 B1 | 6/2002 | McCabe et al. |
| 6,418,344 B1 | 7/2002 | Rezai et al. |
| 6,425,852 B1 | 7/2002 | Epstein et al. |
| 6,463,328 B1 | 10/2002 | John |
| 6,473,639 B1 | 10/2002 | Fischell et al. |
| 6,514,937 B1 | 2/2003 | Mascarenhas |
| 6,539,263 B1 | 3/2003 | Schiff et al. |
| 6,567,696 B2 | 5/2003 | Voznesensky et al. |
| 6,591,138 B1 | 7/2003 | Fischell et al. |
| 6,592,509 B1 | 7/2003 | Hunter, Jr. |
| 6,594,880 B2 | 7/2003 | Elsberry |
| 6,597,954 B1 | 7/2003 | Pless et al. |
| 6,609,030 B1 | 8/2003 | Rezai et al. |
| 6,609,031 B1 | 8/2003 | Law et al. |
| 6,620,151 B2 | 9/2003 | Blischak et al. |
| 6,629,973 B1 | 10/2003 | Wardell et al. |
| 6,666,845 B2 | 12/2003 | Hooper et al. |
| 6,735,474 B1 | 5/2004 | Loeb et al. |
| 6,735,475 B1 | 5/2004 | Whitehurst et al. |
| 6,782,292 B2 | 8/2004 | Whitehurst |
| 6,871,098 B2 | 3/2005 | Nuttin et al. |
| 2001/0027599 A1 | 10/2001 | Elsberry |
| 2002/0013612 A1 | 1/2002 | Whitehurst |
| 2002/0042563 A1 | 4/2002 | Becerra et al. |
| 2002/0058867 A1 | 5/2002 | Breiter et al. |
| 2002/0062143 A1 | 5/2002 | Baudino et al. |
| 2002/0091419 A1 | 7/2002 | Firlik et al. |
| 2002/0099256 A1 | 7/2002 | Manne |
| 2002/0151939 A1 | 10/2002 | Rezai |
| 2002/0169485 A1 | 11/2002 | Pless et al. |
| 2002/0177882 A1 | 11/2002 | DiLorenzo |
| 2002/0193684 A1 | 12/2002 | Anderson et al. |
| 2003/0028072 A1 | 2/2003 | Fischell et al. |
| 2003/0032001 A1 | 2/2003 | Broderick |
| 2003/0036781 A1 | 2/2003 | Nuttin et al. |
| 2003/0097159 A1 | 5/2003 | Schiff et al. |
| 2003/0149457 A1 | 8/2003 | Tcheng et al. |
| 2003/0181954 A1 | 9/2003 | Rezai |
| 2004/0092010 A1 | 5/2004 | Ruiz I Altaba et al. |
| 2005/0033379 A1 | 2/2005 | Lozano et al. |
| 2005/0143799 A1 | 6/2005 | Black et al. |
| 2005/0143800 A1 | 6/2005 | Lando et al. |

OTHER PUBLICATIONS

Ballantine et al., "Stereotaxic Anterior Cingulotomy for Neuropsychiatric Illness and Intractable Pain," J Neurosurg. May 1967;26(5):488-95. No abstract available. PMID: 5337. cited by other.

Barbas et al, "Projections from the Amygdala to Basoventral and Mediodorsal Prefrontal Regions in the Rhesus Monkey," The Journal of Comparative Neurology vol. 300, 1990, pp. 549-571. cited by other.

Barbas et al, "Topographically Specific Hippocampal Projections Target Functionally Distinct Prefrontal Areas in the Rhesus Monkey," Hippocampus vol. 5, 1995, pp. 511-533. cited by other.

Bjorklund et al, "Cell Replacement therapies for Central Nervous System Disorders," Nature Neuroscience vol. 3, No. 6, Jun. 2000, pp. 537-544. cited by other.

Bremner, J.D., "Structural Changes in the Brain in Depression and relationship to Symptom Recurrence," CNS Spectrums, vol. 7, No. 2, Feb. 2002, pp. 129-139. cited by other.

Brent A. Vogt, "Pain and Emotion Interactions in Subregions of the Cingulate Gyrus", vol. 6, Jul. 2005, Nature Reviews/Neuroscience, pp. 533-544. cited by examiner.

Caetano et al, "Anatomical MRI Study of Hippocampus and Amygdala in Patients with Current and Remitted Major Depression," Psychiatry Research: Neuroimaging vol. 132, 2004, pp. 141-147. cited by other.

Capel et al., "The influence of electrostimulation on hexobarbital induced loss of righting reflex in rats," Acupunct. Electrother. Res., 7(1): 17-26, 1982. cited by other.

Cassidy et al., "Frontal Cigulotomy for Affective Disorders," Part V: The Neurophysiologic Model, Chap. 20, 269-275. cited by other.

Cosgrove et al, "Psychosurgery," Neurosurgery Clinicis of North America vol. 6 No. 1, Jan. 1995, pp. 167-176. cited by other.

Delbello et al, "Magnetic Resonance Imaging Analysis of Amygdala and other Subcortical Brain Regions in Adolescents with Bipolar Disorders," Bipolar Disorders vol. 6, 2004, pp. 43-52. cited by other.

Diamond et al, "Preclinical Research on Stress, Memory and the Brain in the Development of Pharmacotherapy for Depression," European Neuropsychopharmacology vol. 14, 2004, pp. S491-S495. cited by other.

Dougherty et al., "Cerebral metabolic correlates as potential predictors of response to anterior cingulotomy for treatment of major depression," J. Neurosurg., 99(6): 1010-7, 2003. cited by other.

Drevets et al, "Functional Anatomical Correlates of Antidepressants Drug Treatment Assessed Using PET Measures of Regional Glucose Metabolism," European Neuropsychopharmacology vol. 12, 2002, pp. 527-544. cited by other.

Drevets et al, "Subgenual Prefrontal Cortex Abnormalities in Mood Disorders," Nature vol. 386, Apr. 24, 1997, pp. 824-827. cited by other.

Ebmeler et al, "Cerebral Perfusion Correlates of Depressed Mood," British Journal of Psychiatry vol. 178, 1997, pp. 77-81. cited by other.

Escobedo et al, "Chronic stimulation of the cingulum in humans with behavior disorders," Surgical Approaches in Psychiatry; MTP, Lancaster, GB, 1973, 66-68. cited by other.

Flor-Henry, "Psychiatric Surgery—1935-1973 Evolution and Current Perspectives," Canadian Psychiatric Association J., 20(2), 157-167, 1975. cited by other.

Fossati et al, "Neuroplasticity: from MRI to depressive Symptoms," European Neuropsychophamacology vol. 14, 2004, pp. S503-S510. cited by other.

Galynker et al, "Hypofrontality and Negative Symptoms in Major Depressive Disorder," The Journal of Nuclear Medicine vol. 39, No. 4, Apr. 1998, pp. 608-612. cited by other.

George A. Mashour, et al., "Psychosurgery: past, present, and future," Brain Research News, www.elsevier.com/locate/brainresrev, 2004, pp. 409-419, Brain Research Reviews 49, (1005), Elsevier B.V., Science Direct. cited by other.

George, Mark S., M.D. et al.; "Brain Activity During Transient Sadness and Happiness in Healthy Women"; American Journal of Psychiatry 152:3, Mar. 1995. cited by other.

Goldapple et al, "Modulation of Cortical-Limbic Pathways in Major Depression," Arch Gen Psychiatry vol. 61, Jan. 2004, pp. 34-41. cited by other.

Haberler et al, "No Tissue Damage by Chronic Deep Brain Stimulation in Parkinson's Disease," Annals of Neurology vol. 48 No. 3, Sep. 2000, pp. 372-376. cited by other.

Haldane et al, "New Insights Help Define the Pathophysiology of Bipolar Affective Disorder: Neuroimaging and Neuropathology Findings," Progress in Neuro-Psychopharmacology & Biological Psychiatry vol. 28, 2004, pp. 943-960. cited by other.

Hilty et al, "A Review of Bipolar Disorder Among Adults," Psychiatric Services vol. 50, 1999, pp. 201-213. cited by other.

Huerta et al, "Low-Frequency Stimulation at the Troughs of .theta.-Oscillation Induces Long-term Depression of Previously Potentiated CA1 Synapses," Journal of Neurophysiology vol. 75, No. 2, Feb. 1996, pp. 877-884. cited by other.

J. Vilkki, "Late Psychologicaland Clinical Effects of Subrostral Cingulotomy and Anterior Mesoloviotomy in Psychiatric Illness," World Congress of Psychiatric Surgery, 4.sup.th ,.Madrid, Spain, Neurosurgical Treatment in Psychiatry, Pain and Epilepsy, 1975, pp. 251-259, University Park Press, Baltimore, Maryland. cited by other.

Jimenez et al., "A Patient with a Resistant Major Depression Disorder Treated with Deep Brain Stimulation in the Inferior Peduncle," Neurosurgery, 57(3): 585-593, 2005. cited by other.

Juhani Vilkki, "Changes in Complex Perception and Memory After Three Different Psychosurgical Operations," Neuropsychologia, vol. 19, No. 4, pp. 553-563, 1981, Pergamon Press Ltd., Great Britain. cited by other.

Kalyanaraman et al., "Stereotaxic Basofrontal Tractotomy," Neurology India, vol. XXI No. 3, Sep. 1973, 113-118. cited by other.

Keightley et al., "An fMRI study investigating cognitive modulation of brain regions associated with emotional processing of visual stimuli," Neuropsychologia, 41(5): 585-96, 2003. cited by other.

Keightley et al., "Personality influences limbic-cortical interactions during sad mood induction," Neuroimage, 20(4): 2031-9, 2003. cited by other.

Kelly et al., "Stereotactic Limbic Leucotomy: A Preliminary Report on Forty Patients," Brit., J. Psychiat. (1973), 123, 141-148. cited by other.

Kelly et al., "Stereotactic Limbic Leucotomy: Neurophysiological Aspects and Operative Technique," Brit. J. Psychiat. (1973), 123, 133-140. cited by other.

Kelly, "Psychosurgery and the limbic system," Postgraduate Medical J., 49, 825-833, 1973. cited by other.

Kennedy et al., "Changes in regional brain glucose metabolism measured with positron emission tomography after paroxetine treatment of major depression," Am. J. Psychiatry, 158(6): 899-905, 2001. cited by other.

Laitinen et al, "Observations on the transcallosal emotional connections," Surgical Approaches in Psychiatry; MTP, Lancaster, GB, 1973, 74-80. cited by other.

Laitinen et al., "Rostral Cingulotomy for Psychiatric Disorders: Electrophysiological, Psychological and Clinical Findings," Vopr Neirokhir. Jan.-Feb. 1973; 37(1) 23-30 (original Russian version and translation provided). cited by other.

Laitinen, "Emotional Responses to Subcortical Electrical Stimulation in Psychiatric Patients," Clin. Neurol. Neurosurg. 1979. vol. 81-3, 148-157. cited by other.

Laitinen, "Psychosurgery Today," Acta Neurochirurgica, 1988, Supp. 44, 158-162. Review. cited by other.

Laitinen, "Psychosurgery," Sterotact Funct Neurosurg 2001; 76:239-242. Review. cited by other.

Laitinen, "Stereotactic Lesions in the Knee of the Corpus Callosum in the Treatment of Emotional Disorders," The Lancet, Feb. 26, 1972, 472-475. cited by other.

Lange et al, "Enlarged Amygdala Volume and Reduced Hippocampal Volume in Young Women with Major Depression," Psychological Medicine vol. 34, 2004, pp. 1059-1064. cited by other.

Lauri V. Laitinen, et al., "Stereotaxic Ventral Anterior Cingulotomy in Some Psychological Disorders," Psychosurgery, Proceedings of the Second International Conference on Psychosurgery Held on Copenhagen, Denmark, 1972, pp. 242-252, Charles C. Thomas Publisher, Springfield, IL. cited by other.

Lewin, "Selective leucotomy: A review," Surgical Approaches in Psychiatry; MTP (Medical and Tech. Publishing Co. Ltd.), Lancaster, GB, 1973, 69-73. cited by other.

Liotti et al, "Differential Limbic-Cortical Correlates of Sadness and Anxiety in Healthy Subjects: Implications for Affective Disorders," Society of Biological Psychiatry vol. 48, 2000, pp. 30-42. cited by other.

Liotti et al., "The role of functional neuroimaging in the neuropsychology of depression," J. Clin. Exp. Neuropsychol., 23(1): 121-36, 2001. cited by other.

Liotti et al., "Unmasking disease-specific cerebral blood flow abnormalities: mood challenge in patients with remitted unipolar depression," Am. J. Psychiatry, 159(11): 1830-40, 2002. cited by other.

Little et al, "How Common is Resistance to Treatment in Recurrent, Nonpsychotic Geriatric Depression?", American Journal of Psychiatry 155:8, Aug. 1998, pp. 1035-1038. cited by other.

Mayberg et al, "Reciprocal Limbic-Cortical Function and Negative Mood: Converging PET Findings in Depression and Normal Sadness," Am J. Psychiatry 156:May 5, 1999, pp. 675-682. cited by other.

Mayberg et al, "Regional Metabolic Effects of Fluoxetine in Major Depression: Serial Changes and Relationship to Clinical Response," Biological Psychiatry vol. 48, 2000, pp. 830-843. cited by other.

Mayberg et al., "Cingulate function in depression: a potential predictor of treatment response," Neuroreport, 8(4): 1057-61, 1997. cited by other.

Mayberg et al., "Deep brain stimulation for treatment-resistant depression," Neuron, 45(5): 651-60, 2005. cited by other.

Mayberg et al., "Depression in Parkinson's disease: a biochemical and organic viewpoint," Adv. Neurol., 65: 49-60, 1995. cited by other.

Mayberg et al., "Paralimbic frontal lobe hypometabolism in depression associated with Huntington's disease," Neurology, 42(9): 1791-7, 1992. cited by other.

Mayberg et al., "Paralimbic hypoperfusion in unipolar depression," J. Nucl. Med., 35(6): 929-34, 1994. cited by other.

Mayberg et al., "The Functional Neuroanatomy of the Placebo Effect," American Journal of Psychiatry vol. 159, 2002, pp. 728-737. cited by other.

Mayberg, "Clinical correlates of PET- and SPECT-identified defects in dementia," J. Clin. Psychiatry, 55 Suppl.: 12-21, 1994. cited by other.

Mayberg, "Depression, II: localization of pathophysiology," Am. J. Psychiatry, 159(12): 1979, 2002. cited by other.

Mayberg, "Frontal lobe dysfunction in secondary depression," J. Neuropsychiatry Clin. Neurosci., 6(4): 428-42, 1994. cited by other.

Mayberg, "Position emission tomography imaging in depression: a neural systems perspective," Neuroimaging Clin. N. Am., 13(4): 805-15, 2003. cited by other.

Mayberg, Helen, "Modulating Dysfunctional Limbic-Cortical Cicuits in Depression: towards development of brain-based algorithms for diagnosis and optimised treatment," British Medical Bulletin vol. 65, 2003, pp. 193-207. cited by other.

Mayberg, Helen, "Modulating Limbic-Cortical Circuits in Depression: Targets of Antidepressant Treatments," Seminars in Clinical Neuropsychiatry vol. 7, No. 4, Oct. 2002, pp. 255-268. cited by other.

Mayberg, Helen; "Limbic-Cortical Dysregulation: A Proposed Model of Depression," Journal of Neuropsychiatry vol. 9 No. 3, 1997, pp. 471-481. cited by other.

Meyer et al, "Stereotactic cingulotomy with results of acute stimulation and serial psychological testing," Surgical Approaches in Psychiatry; MTP, Lancaster, GB, 1973, 39-58. cited by other.

Ortiz, "The role of the limbic lobe in central pain mechanisms, an hypothesis relating to the gate control theory of pain," Surg Approaches in Psych; MTP, Lancaster GB, 59-64. cited by other.

Patterson et al., "Electrostimulation: addiction treatment for the coming millennium," J. Altern. Complement Med., 2(4): 485-91, 1996. cited by other.

Patterson, "Effects of neuro-electric therapy (N.E.T.) in drug addiction: interim report," Bull. Narc., 25(4): 55-62, 1976. cited by other.

Patterson, "Electrostimulation and opiate withdrawal," Br. J. Psychiatry, 146: 213, 1985. cited by other.

Patterson, "Electrotherapy: addictions and neuroelectric therapy," Nurs. Times, 75(48): 2080-3, 1979. cited by other.

Patterson, "Neuro-electric therapy: criticisms of the 1984 Bethlem Study," Br. J. Addict., 84(7): 818, 1989. cited by other.

Phillips et al, "Neurobiology of Emotion Perception I: The Neural Basis of Normal Emotion Perception," Biol Psychiatry vol. 54, 2003, pp. 504-514. cited by other.

Phillips et al, "Neurobiology of Emotion Preception II: Implications for Major Psychiatric Disorders," Biol Psychiatry vol. 54, 2003, pp. 515-528. cited by other.

Rauch, S. L., "Neuroimaging and Neurocircuitry Models Pertaining to the Neurosurgical Treatment of Psychiatric Disorders," Neurosurg Clin N Am vol. 14, 2003, pp. 213-223. cited by other.

Richardson, "Stereotactic Lesions in the Knee of the Corpus Callosum in the Treatment of Emotional Disorders," Lancet. Mar. 11, 1972; 1 (7750): 591-592. cited by other.

Richardson, "Stereotactic Limbic Leucotomy: Surgical Technique," Postgraduate Medical J., (Dec. 1973) 49, 860-864. cited by other.

Sander et al, "The Human Amygdala: An Evolved System for Relevance Detection," Reviews in Neurosciences vol. 14, 2003, pp. 303-316. cited by other.

Scoville, "Neurosurgical Forum-Letters to the Editor," J. Neurosurg., vol. 38, Apr. 1973, 535-536. cited by other.

Seminowicz et al, "Limbic-frontal Circuitry in Major Depression: A Path Modeling Metanalysis," NeuroImage vol. 22, 2004, pp. 409-418. cited by other.

Sheline, Yvette, "3D MRI Studies of Neuroanatomic Changes in Unipolar Major Depression: The Role of Stress and Medical Comorbidity," Biol Psychiatry vol. 48, 2000, pp. 791-800. cited by other.

Soares et al, "The Functional Neuroanatomy of Mood Disorders," J. Psychiat. Res. vol. 31 No. 4, 1997, pp. 393-432. cited by other.

Starkstein et al., "Depression and cognitive impairment in Parkinson's disease," Brain, 112 (Pt. 5): 1141-53, 1989. cited by other.

Stefurak et al., "Deep brain stimulation for Parkinson's disease dissociates mood and motor circuits: a functional MRI case study," Mov. Disord., 18(12): 1508-16, 2003. cited by other.

Temple, Sally, "Stem Cell Plasticity—Building the Brain of Our dreams," Nature Reviews/Neuroscience vol. 2, Jul. 2001, pp. 513-520. cited by other.

Velasco et al., "Neurobiological Background for Performing Surgical Intervention in the Inferior Thalmic Peduncle for Treatment of Major Depression Disorders," Neurosurgery, 57(3): 439-448, 2005. cited by other.

Videbech et al, "Hippocampal Volume and Depression: A Meta-Analysis of MRI Studies," Am. J. Psychiatry vol. 161, No. 11, Nov. 2004, pp. 1957-1966. cited by other.

Vogt, Brent A.; "Pain and Emotion Interactions in Subregions of the Cingulate Gyrus"; Nature Reviews Neuroscience, vol. 6, Jul. 2005, pp. 533-544. cited by other.

Weissman et al, "Cross-National Epidemiology of Major Depression and Bipolar Disorder," JAMA vol. 276, No. 4, Jul. 24-31, 1996, pp. 293-299. cited by other.

Whalen, Paul J. et al.; "Masked Presentations of Emotional Facial Expressions Modulate Amygdala Activity without Explicit Knowledge"; Journal of Neuroscience, Jan. 1, 1998, 18(1):411-418. cited by other.

Yudofsky et al., "Neurosurgical and Related Interventions for the Treatment of Patients With Psychiatric Disorders," J. of Neuropsychiatry, vol. 2, #3, Summer 1990, 253-255. cited by other.

* cited by examiner

METHOD OF TREATING DEPRESSION, MOOD DISORDERS AND ANXIETY DISORDERS USING NEUROMODULATION

CROSS-REFERENCE TO RELATED APPLICATIONS

The present application is a continuation of U.S. patent application Ser. No. 10/872,277, filed Jun. 18, 2004 (which claims priority to U.S. Provisional Application Nos. 60/511,268 filed Oct. 15, 2003 and 60/550,164 filed Mar. 4, 2004, and Canadian Application No. 2,432,810 filed Jun. 19, 2003), all of which is incorporated herein by reference in its entirety.

TECHNICAL FIELD

This application relates to nervous tissue stimulation for treating depression, anxiety disorders and mood disorders, and more particularly to modulating nervous tissue at a predetermined stimulation site in brain tissue.

BACKGROUND

Recent estimates indicate that more than 19 million Americans over the age of 18 years experience a depressive illness each year. The American Psychiatric Association recognizes several types of clinical depression, including Mild Depression (Dysthymia), Major Depression, and Bipolar Disorder (Manic-Depression). Major Depression is defined by a constellation of chronic symptoms that include sleep problems, appetite problems, anhedonia or lack of energy, feelings of worthlessness or hopelessness, difficulty concentrating, and suicidal thoughts. Approximately 9.2 million Americans suffer from Major Depression, and approximately 15 percent of all people who suffer from Major Depression take their own lives. Bipolar Disorder involves major depressive episodes alternating with high-energy periods of rash behavior, poor judgment, and grand delusions. An estimated one percent of the American population experiences Bipolar Disorder annually.

Significant advances in the treatment of depression have been made in the past decade. Since the introduction of selective serotonin reuptake inhibitors (SSRIs), i.e., Prozac®, many patients have been effectively treated with anti-depressant medication. New medications to treat depression are introduced almost every year, and research in this area is ongoing. However, an estimated 10 to 30 percent of depressed patients taking an anti-depressant are partially or totally resistant to the treatment. Those who suffer from treatment-resistant depression have almost no alternatives. Thus, there is a need to develop alternative treatments for these patients.

The use of electrical stimulation for treating neurological disease, including such disorders as movement disorders including Parkinson's disease, essential tremor, dystonia, and chronic pain, has been widely discussed in the literature. It has been recognized that electrical stimulation holds significant advantages over lesioning since lesioning destroys the nervous system tissue. In many instances, the preferred effect is to modulate neuronal activity. Electrical stimulation permits such modulation of the target neural structures and, equally importantly, does not require the destruction of nervous tissue. Such electrical stimulation procedures include electroconvulsive therapy (ECT), repetitive transcranial (rTMS) magnetic stimulation and vagal nerve stimulation (VNS).

Efforts have been made to treat psychiatric disorders with peripheral/cranial nerve stimulation. Recently, partial benefits with vagus nerve stimulation in patients with depression have been described in U.S. Pat. No. 5,299,569. Another example of electrical stimulation to treat depression is described in U.S. Pat. No. 5,470,846, which discloses the use of transcranial pulsed magnetic fields to treat depression. Yet further, U.S. Pat. No. 5,263,480 describes that stimulation of the vagus nerve may control depression and compulsive eating disorders and U.S. Pat. No. 5,540,734 teaches stimulation of the trigeminal or glossopharyngeal nerves for psychiatric illness, such as depression.

Deep brain stimulation (DBS) has been applied to the treatment of central pain syndromes and movement disorders, and it is currently being explored as a therapy for epilepsy. For instance, U.S. Pat. No. 6,016,449 and U.S. Pat. No. 6,176,242 disclose a system for the electrical stimulation of areas in the brain for the treatment of certain neurological diseases such as epilepsy, migraine headaches and Parkinson's disease.

Various electrical stimulation and/or drug infusion devices have been proposed for treating neurological disorders. Some devices stimulate through the skin, such as electrodes placed on the scalp. Other devices require significant surgical procedures for placement of electrodes, catheters, leads, and/or processing units. These devices may also require an external apparatus that needs to be strapped or otherwise affixed to the skin.

However, despite the aforesaid available treatments, there are patients with major depression that remain treatment refractory and chronically disabled. For these severely ill and disabled patients, novel therapies are required.

SUMMARY

The present application relates to electrical and/or chemical stimulation applied to areas of the brain not considered in the prior art to play a role in depression. In certain embodiments, the application uses electrical stimulation and/or chemical stimulation (i.e., one or more pharmaceuticals) to treat depression. In addition to electrical and/or chemical stimulation, magnetic stimulation can also be used, such as transcranial magnetic stimulation ("TMS"). According to one representative embodiment, the stimulation modulates areas of the brain that exhibit altered activity in patients relative to psychiatrically normal control subjects, thereby treating or preventing affective disorders, for example depression and/or anxiety disorders. Such stimulation is likely to be produced by electrical stimulation, an excitatory neurotransmitter agonist(s) (i.e., norepinephrine), an inhibitory neurotransmitter antagonist(s), and/or a medication that increases the level of an excitatory neurotransmitter (i.e., flouxetine (Prozac®), trazodone).

One representative embodiment utilizes neurosurgical intervention to modulate the pathological activity of a subcallosal area in patients suffering from depression or other affective disorders. Such interventions include, applying electrical stimulation, herein termed "deep brain stimulation" or DBS, as is currently practiced to treat a number of disorders like Parkinson's disease. Other stimulations can include chemical stimulation such as through the use of pharmaceutical or drug pumps, for example local delivery of neuroactive substances to disrupt or block the pathological activity stemming from or coursing through this area. It is envisioned that such stimulation (i.e., electrical, magnetic and/or chemical) modulates the gray matter and white matter tracts in a subcallosal area, as well as the white matter tracts that are associated with the subcallosal area (such as the white matter tracts that lead to and from the subcallosal area or that are adjacent to the subcallosal area), which in turn modulates the limbic system. Still further, other stimulations may comprise magnetic stimulation and/or transplantation of cells.

Certain embodiments involve a method that comprises surgically implanting a device or stimulation system in communication with a predetermined site, for example a subcallosal area. The device or stimulation system is operated to stimulate the predetermined site thereby treating the mood and/or anxiety disorder. The device or stimulation system may include a probe, for example, an electrode assembly (i.e., electrical stimulation lead), pharmaceutical-delivery assembly (i.e., catheters) or combinations of these (i.e., a catheter having at least one electrical stimulation lead) and/or a signal generator or signal source (i.e., electrical signal source, chemical signal source (i.e., pharmaceutical delivery pump) or magnetic signal source). The probe may be coupled to the electrical signal source, pharmaceutical delivery pump, or both which, in turn, is operated to stimulate the predetermined treatment site. Yet further, the probe and the signal generator or source can be incorporated together, wherein the signal generator and probe are formed into a unitary or single unit, such unit may comprise, one, two or more electrodes. These devices are known in the art as microstimulators, for example, Bion™ which is manufactured by Advanced Bionics Corporation.

It is envisioned that the predetermined site is a subcallosal area. A subcallosal area includes, but is not limited to subgenual cingulate area, subcallosal cingulate area, ventral/medial prefrontal cortex area, ventral/medial white matter, Brodmann area 24, Brodmann area 25, and/or Brodmann area 10. More specifically, the predetermined site is a subgenual cingulate area, more preferably Brodmann area 25/Brodmann area 24.

Stimulation of a subcallosal area includes stimulation of the gray matter and white matter tracts associated with the subcallosal area that results in an alleviation or modulation of the mood and/or anxiety disorder. Associated white matter tracts includes the surrounding or adjacent white matter tracts leading to or from a subcallosal area or white matter tracts that are contiguous with the subcallosal area. Modulating the subcallosal area via electrical and/or chemical stimulation (i.e., pharmaceutical) and/or magnetic stimulation can result in increasing, decreasing, masking, altering, overriding or restoring neuronal activity resulting in treatment of the mood and/or anxiety disorder. Yet further, stimulation of a subcallosal area may result in modulation of neuronal activity of other areas of the brain, for example, Brodmann area, 24, Brodmann area 25, Brodmann area 10, Brodmann area 9, the hypothalamus and the brain stem.

Another representative embodiment comprises a method of treating the mood and/or anxiety disorder comprising the steps of: surgically implanting an electrical stimulation lead having a proximal end and a stimulation portion, wherein after implantation the stimulation portion is in communication with a predetermined site; the stimulation lead is coupled to or in communication with a signal generator; and an electrical signal is generated using the signal generator to modulate the predetermined site thereby treating the mood and/or anxiety disorder. The mood disorder is selected from the group consisting of major depressive disorder, bipolar disorder, and dysthymic disorder. The anxiety disorder is selected from the group consisting of panic disorder, posttraumatic stress disorder, obsessive-compulsive disorder and phobic disorder.

In further embodiments, the method can comprise the steps of: surgically implanting a catheter having a proximal end coupled to a pump and a discharge portion for infusing a dosage of a pharmaceutical, wherein after implantation the discharge portion of the catheter is in communication with the predetermined stimulation site; and operating the pump to discharge the pharmaceutical through the discharge portion of the catheter into the stimulation site thereby treating the mood and/or anxiety disorder. The pharmaceutical is selected from the group consisting of inhibitory neurotransmitter agonist, an excitatory neurotransmitter antagonist, an agent that increases the level of an inhibitory neurotransmitter, an agent that decrease the level of an excitatory neurotransmitter, and a local anesthetic agent. It is envisioned that chemical stimulation or pharmaceutical infusion can be preformed independently of electrical stimulation and/or in combination with electrical stimulation.

Another representative embodiment is a method of treating a mood and/or anxiety disorder comprising the steps of: surgically implanting an electrical stimulation lead having a proximal end and a stimulation portion, wherein after implantation the stimulation portion is in communication with a predetermined site; surgically implanting a catheter having a proximal end coupled to a pump and a discharge portion for infusing a dosage of a pharmaceutical, wherein after implantation the discharge portion of the catheter is in communication with a predetermined infusion site; and coupling the proximal end of the lead to a signal generator; generating an electrical signal with the signal generator to modulate the predetermined site; and operating the pump to discharge the pharmaceutical through the discharge portion of the catheter into the infusion site thereby treating the mood and/or anxiety disorder.

Other representative embodiments include a system for treating subjects with mood and/or anxiety disorders. The therapeutic system comprises an electrical stimulation lead that is implanted into the subject's brain. The electrical stimulation lead comprises at least one electrode that is in communication with a predetermined site and delivers electrical signals to the predetermined site in response to received signals; and a signal generator that generates signals for transmission to the electrodes of the lead resulting in delivery of electrical signals to predetermined site thereby treating the mood and/or anxiety disorder. The electrical stimulation lead may comprise one electrode or a plurality of electrodes in or around the target area. Still further, the signal generator is implanted in the subject's body.

Another example of a therapeutic system is a catheter having a proximal end coupled to a pump and a discharge portion for infusing a dosage of a pharmaceutical, wherein after implantation the discharge portion of the catheter is in communication with a predetermined stimulation site; and a pump to discharge the pharmaceutical through the discharge portion of the catheter into the predetermined stimulation site thereby treating the mood and/or anxiety disorder.

Still further, another therapeutic system comprises a device that is surgically implanted into the subject such that the device is in communication with a predetermined site, for example a subcallosal area. An exemplary device includes a microstimulator (i.e., Bion™ manufactured by Advanced Bionics Corporation) in which the device contains a generating portion and at least one electrode in a single unit. In further embodiments, a lead assembly is associated with at least one electrode of the microstimulator such that the lead can stimulate the predetermined site not in direct contact with the microstimulator.

Other therapeutic systems include a probe that is in communication with the predetermined site and a device that stimulates the probe thereby treating the mood and/or anxiety disorder. The probe can be, for example, an electrode assembly (i.e., electrical stimulation lead), pharmaceutical-delivery assembly (i.e., catheters) or combinations of these (i.e., a catheter having at least one electrical stimulation lead). The probe is coupled to the device, for example, electrical signal source, pharmaceutical delivery pump, or both which, in turn, is operated to stimulate the predetermined treatment site.

The foregoing has outlined rather broadly features and/or technical advantages in order that the detailed description that follows may be better understood. Additional features and advantages will be described hereinafter. It should be appreciated that the conception and specific embodiment disclosed may be readily utilized as a basis for modifying or designing other structures for carrying out the same purposes. It should also be realized that such equivalent constructions do not depart from the appended claims. Novel features, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

For a more complete understanding of some representative embodiments, reference is now made to the following descriptions taken in conjunction with the accompanying drawings.

FIG. 6A shows a T1 MRI in the horizontal plane showing the tips (at arrows) on the implanted lead 4 contact electrodes positioned anterior to the anterior commissure (AC), approximately 7 mm from the midline and below the plane of the inter-commissural line, in a patient with depression.

FIG. 6B shows an axial T1 MRI in the horizontal plane of a patient with depression implanted with chronic deep brain stimulating electrodes to stimulate subcallosal white matter and adjacent cortex including subgenual cingulate gyrus, particularly Brodmann area 25/Brodmann area 24.

FIG. 6C shows a Sagittal T1 weighted MRI, vertical through the nose, showing an implanted chronic deep brain stimulating electrode with 4 contacts to stimulate subcallosal white matter and adjacent cortex including subgenual cingulate gyrus, particularly Brodmann area 25/Brodmann area 24. The central dot shows a contact area. FIG. 6D shows a T1 weighted MRI Coronal view of a patient having scans of FIGS. 6A and 6B showing right and left electrodes in the plane of the brain corresponding to the Schaltebrand and Warren atlas section plate 3 shown in FIG. 3. The central dot is the midline. FIG. 6E shows T1 weighted MRI images of a second patient with bilateral electrodes implanted to stimulate subcallosal white matter and adjacent cortex including subgenual cingulate gyrus, particularly Brodmann area 25/Brodmann area 24.

DETAILED DESCRIPTION

Figure 1:
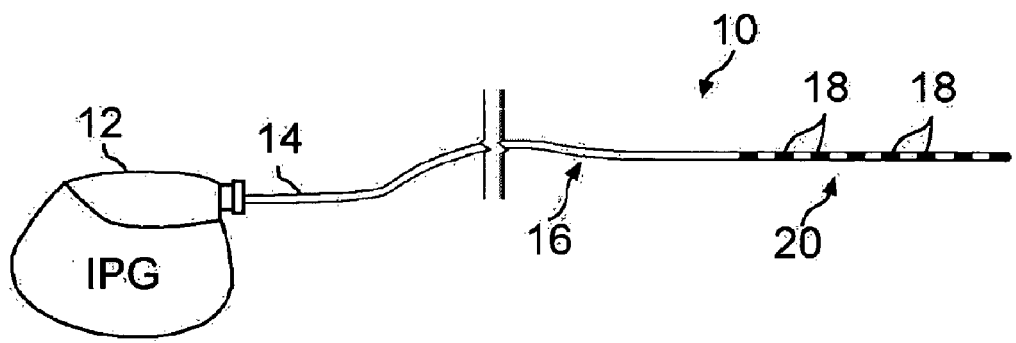
FIGS. 1A and 1B illustrate example electrical stimulation systems.
Figure 1:
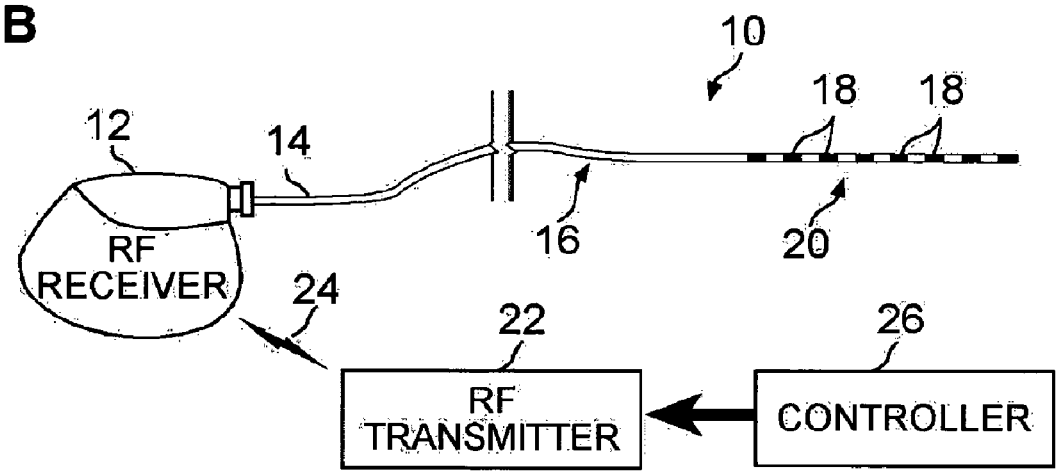
Figure 2:
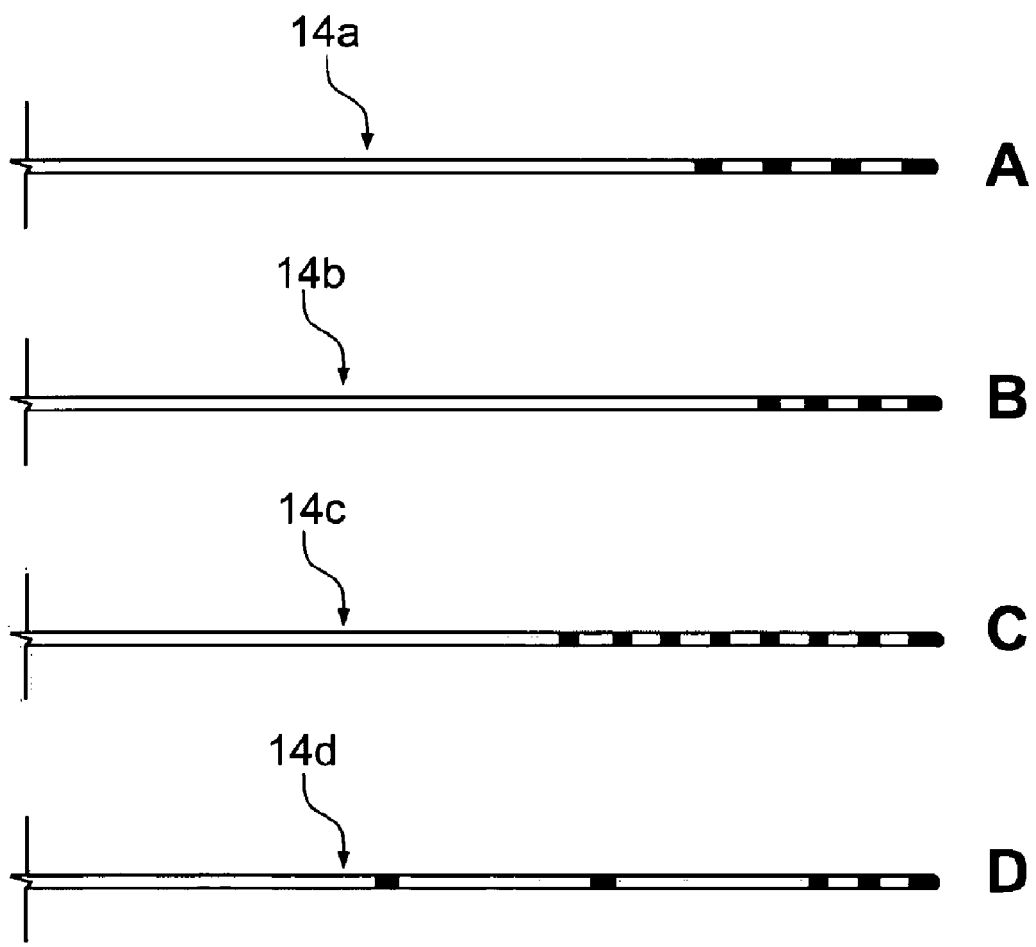
FIGS. 2A-2D illustrate example electrical stimulation leads that may be used to stimulate a patient according to some representative embodiments.

It is readily apparent to one skilled in the art that various embodiments and modifications can be made to the representative embodiments in this application without departing from the scope of the appended claims.

I. DEFINITIONS

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein the term "affective disorders" refers to a group of disorders that are commonly associated with co-morbidity of depression and anxiety symptoms.

As used herein the term "anxiety" refers to an uncomfortable and unjustified sense of apprehension that may be diffuse and unfocused and is often accompanied by physiological symptoms.

As used herein the term "anxiety disorder" refers to or connotes significant distress and dysfunction due to feelings of apprehension, guilt, fear, etc. Anxiety disorders include, but are not limited to panic disorders, posttraumatic stress disorder, obsessive-compulsive disorder and phobic disorders.

As used herein, the term "Brodmann area 25" refers to the defined area of Brodmann area 25 as known by one of skill in the art, as well as the surrounding or adjacent white matter tracts leading to and from Brodmann area 25 and/or white matter tracts that are contiguous with Brodmann area 25. The surrounding or adjacent white matter can include up to approximately a 1 cm radius of Brodmann area 25.

As used herein, the term "Brodmann area 24" refers to the defined area of Brodmann area 24 as known by one of skill in the art, as well as the surrounding or adjacent white matter tracts leading to and from Brodmann area 24 and/or white matter tracts that are contiguous with Brodmann area 24. The surrounding or adjacent white matter can include up to approximately a 1 cm radius of Brodmann area 24.

As used herein, the term "Brodmann area 9" refers to the defined area of Brodmann area 9 as known by one of skill in the art, as well as the surrounding or adjacent white matter tracts leading to and from Brodmann area 9 and/or white matter tracts that are contiguous with Brodmann area 9. The surrounding or adjacent white matter can include up to approximately a 1 cm radius of Brodmann area 9.

As used herein, the term "Brodmann area 10" refers to the defined area of Brodmann area 10 as known by one of skill in the art, as well as the surrounding or adjacent white matter tracts leading to and from Brodmann area 10 and/or white matter tracts that are contiguous with Brodmann area 10. The surrounding or adjacent white matter can include up to approximately a 1 cm radius of Brodmann area 10.

As used herein the term "depression" refers to a morbid sadness, dejection, or melancholy.

As used herein, the term "in communication" refers to one or more electrical stimulation leads and/or catheters being adjacent, in close proximity, or directly next to, or in direct contact or directly in the predetermined stimulation site. Thus, one of skill in the art understands that the one or more electrical stimulation leads and/or catheters are "in communication" with the predetermined site of the brain if the stimulation results in a modulation of neuronal activity associated with a site. Still further, "in communication" with brain tissue encompasses surrounding or adjacent white matter tracts or fibers leading to and from the brain tissue and/or white matter tracts or fibers that are contiguous with the brain tissue.

As used herein the term "limbic system" encompasses the amygdala, hippocampus, septum, cingulate gyrus, cingulate cortex, hypothalamus, epithalamus, anterior thalamus, mammillary bodies, and fornix. The limbic system has connections throughout the brain, more particularly with the primary sensory cortices, including the rhinencephalon for smell, the autonomic nervous system via the hypothalamus, and memory areas. Yet further, the limbic system is involved in mood, emotion and thought.

As used herein the term "mania" or "manic" refers to a disordered mental state of extreme excitement.

As used herein the term "mood" refers to an internal emotional state of a person.

As used herein the term "mood disorder" is typically characterized by pervasive, prolonged, and disabling exaggerations of mood and affect that are associated with behavioral, physiologic, cognitive, neurochemical and psychomotor dysfunctions. The major mood disorders include, but are not limited to major depressive disorder (also known as unipolar disorder), bipolar disorder (also known as manic depressive illness or bipolar depression), dysthymic disorder. Other mood disorders may include, but are not limited to major depressive disorder, psychotic; major depressive disorder, melancholic; major depressive disorder, seasonal pattern; postpartum depression; brief recurrent depression; late luteal phase dysphoric disorder (premenstrual dysphoria); and cyclothymic disorder.

As used herein the term "modulate" refers to the ability to regulate positively or negatively neuronal activity. Thus, the term modulate can be used to refer to an increase, decrease, masking, altering, overriding or restoring neuronal activity. Modulation of neuronal activity affects psychological and/or psychiatric activity of a subject.

As used herein, the term "neuronal" refers to a neuron which is a morphologic and functional unit of the brain, spinal column, and peripheral nerves.

As used herein, the term "pharmaceutical" refers to a chemical or agent that is used as a drug. Thus, the term pharmaceutical and drug are interchangeable.

As used herein, the term "stimulate" or "stimulation" refers to electrical, chemical, and/or magnetic stimulation that modulates the predetermined sites in the brain.

As used herein, the term "subcallosal area" includes the medial gray matter and white matter under the corpus callosum, as well as the white matter tracts that are associated with the subcallosal area. Associated white matter tracts includes the surrounding or adjacent white matter tracts leading to or from a subcallosal area or white matter tracts that are contiguous with the subcallosal area. For the purposes of the present application, the subcallosal area includes the following gray matter and the white matter tracts, as well as the white matter tracts that are associated with or leading to or from the following areas: subgenual cingulate area, subcallosal cingulate area, ventral/medial prefrontal cortex area, ventral/medial white matter, Brodmann area 24, Brodmann area 25, and/or Brodmann area 10. The surrounding or adjacent white matter tracts can include up to approximately a 1 cm radius of the subcallosal area.

As used herein, the term "subgenual cingulate area" includes the gray matter and white matter tracts associated with the subgenual cingulate area, the white matter tracts that surround or adjacent to the subgenual cingulate area, or the white matter tracts that lead to or from the subgenual cingulate area. The subgenual cingulate area includes Brodmann area 25 and the subgenual portion of Brodmann area 24. The surrounding or adjacent white matter can include up to approximately a 1 cm radius of the subgenual cingulate area As used herein, the term "treating" and "treatment" refers to modulating certain areas of the brain so that the subject has an improvement in the disease, for example, beneficial or desired clinical results. For purposes of this application, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. ELECTRICAL STIMULATION DEVICES

FIGS. 1A and 1B illustrate example electrical stimulation systems or devices 10 used to provide deep brain stimulation. Stimulation system 10 generates and applies a stimulus to a target area of the brain, for example, a target area of a subcallosal area, more particularly, a subgenual cingulate area. Still further, the target area can comprise Brodmann area 25 and/or Brodmann area 24. In general terms, stimulation system 10 includes an implantable electrical stimulation source 12 and an implantable electrical stimulation lead 14 for applying the stimulation signal to the target brain tissue. In operation, both of these primary components are implanted in the person's body. Stimulation source 12 is coupled to a connecting portion 16 of electrical stimulation lead 14. Stimulation source 12 controls the electrical signals transmitted to electrodes 18 located on a stimulating portion 20 of electrical stimulation lead 14, located adjacent the target brain tissue, according to suitable signal parameters (i.e., duration, intensity, frequency, etc.). A doctor, the patient, or another user of stimulation source may directly or indirectly input signal parameters for controlling the nature of the electrical stimulation provided.

Another exemplary stimulation system or device includes a microstimulator (i.e., Bion™, manufactured by Advanced Bionics Corporation) in which the device contains a signal generating portion and at least one electrode in a the same unit or single unit, as defined in U.S. Pat. Nos. 6,051,017; 6,735,475 and 6,735,474, each of which are incorporated herein in its entirety. In further embodiments, a lead assembly is associated with at least one electrode of the microstimulator such that the lead can stimulate the predetermined site not in contact with the micro stimulator.

In one embodiment, as shown in FIG. 1A, stimulation source 12 includes an implantable pulse generator (IPG). One of skill in the art is aware that any commercially available implantable pulse generator can be used in the present application, as well as a modified version of any commercially available pulse generator. Thus, one of skill in the art would be able to modify an IPG to achieve the desired results. An exemplary IPG is one that is manufactured by Advanced Neuromodulation Systems, Inc., such as the Genesis® System, part numbers 3604, 3608, 3609, and 3644. Another example of an IPG is shown in FIG. 1B, which shows stimulation source 12 including an implantable wireless receiver. An example of a wireless receiver may be one manufactured by Advanced Neuromodulation Systems, Inc., such as the Renew® System, part numbers 3408 and 3416. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the signal parameters of electrical signals transmitted through electrical stimulation lead 14 to the stimulation site. An example wireless transmitter may be one manufactured by Advanced Neuromodulation Systems, Inc., such as the Renew® System, part numbers 3508 and 3516.

FIGS. 2A through 2D illustrate example electrical stimulation leads 14 that may be used to provide electrical stimulation to an area of the brain, however, one of skill in the art is aware that any suitable electrical lead may be used. As described above, each of the one or more leads 14 incorporated in stimulation system 10 includes one or more electrodes 18 adapted to be positioned near the target brain tissue and used to deliver electrical stimulation energy to the target brain tissue in response to electrical signals received from stimulation source 12. A percutaneous lead 14, such as example leads shown in FIG. 2A-2D, includes one or more circumferential electrodes 18 spaced apart from one another along the length of lead 14. Circumferential electrodes 18 emit electrical stimulation energy generally radially in all directions.

III. IMPLANTATION OF ELECTRICAL STIMULATION DEVICES

While not being bound by the description of a particular procedure, patients who are to have an electrical stimulation lead or electrode implanted into the brain, generally, first have a stereotactic head frame, such as the Leksell, CRW, or Compass, mounted to the patient's skull by fixed screws. However, frameless techniques may also be used. Subsequent to the mounting of the frame, the patient typically undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The current way to do this is to rigidly mount the head frame to the surgical table. Subsequently, a series of reference points are established to relative aspects of the frame and the patient's skull, so that either a person or a computer software system can adjust and calculate the correlation between the real world of the patient's head and the virtual space model of the patient's MRI scans. The surgeon is able to target any region within the stereotactic space of the brain with precision (i.e., within 1 mm). Initial anatomical target localization is achieved either directly using the MRI images, or indirectly using interactive anatomical atlas programs that map the atlas image onto the stereotactic image of the brain. As is described in greater detail below, the anatomical targets may be stimulated directly or affected through stimulation in another region of the brain.

Figure 3:
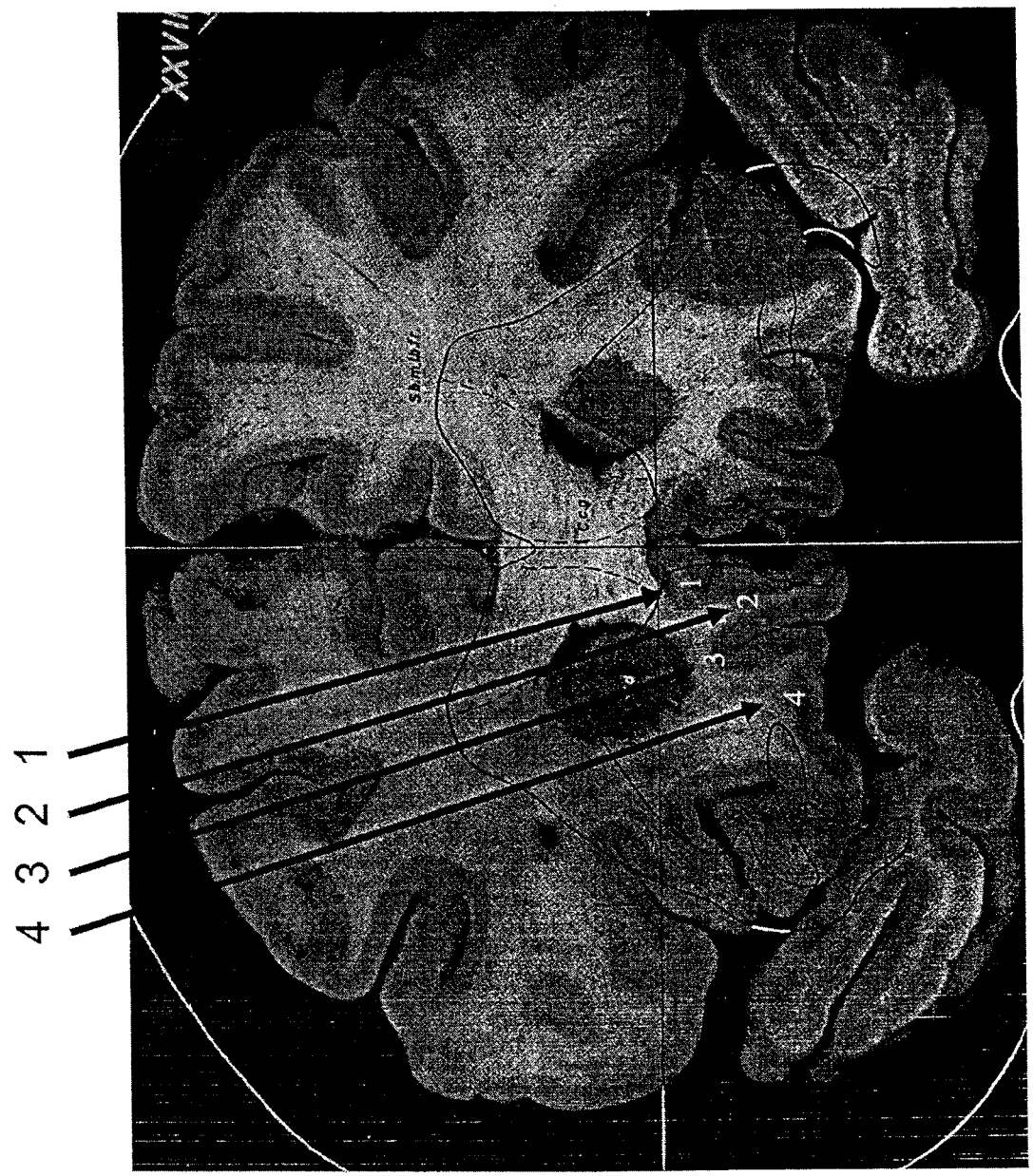
FIG. 3 is a coronal (front vertical) section of a human brain showing arrows directed to target areas.

With reference to FIG. 3, this shows the position of the subcallosal area having coordinates derived from the Schaltenbrand and Wahren Atlas plate 3 coronal section through the brain are 6-7 mm from the midline (range 2-14 mm), 29 mm anterior to the mid-commissural point range (20-40) and 5 mm (range 0-10 mm) below the intra-commissural line. Referring to FIG. 3, arrow 1 points to the subgenual cingulate area, more particularly Brodmann area 25; arrow 2 points to the gyrus rectus area; arrow 3 points to the subcaudate area; and arrow 4 points to the orbitofrontal area.

Based upon the coordinates derived or described above, the electrical stimulation lead 14 can be positioned in the brain. Typically, an insertion cannula for electrical stimulation lead 14 is inserted through the burr hole into the brain, but a cannula is not required. For example, a hollow needle may provide the cannula. The cannula and electrical stimulation lead 14 may be inserted together or lead 14 may be inserted through the cannula after the cannula has been inserted.

Once an electrical stimulation lead, such as lead 14, has been positioned in the brain, the lead is uncoupled from any stereotactic equipment present, and the cannula and stereotactic equipment are removed. Where stereotactic equipment is used, the cannula may be removed before, during, or after removal of the stereotactic equipment. Connecting portion 16 of electrical stimulation lead 14 is laid substantially flat along the skull. Where appropriate, any burr hole cover seated in the burr hole may be used to secure electrical stimulation lead 14 in position and possibly to help prevent leakage from the burr hole and entry of contaminants into the burr hole. Example burr hole covers that may be appropriate in certain embodiments are illustrated and described in co-pending U.S. Application Nos. 60/528,604 and 60/528,689, both filed Dec. 11, 2003 and entitled "Electrical Stimulation System and Associated Apparatus for Securing an Electrical Stimulation Lead in Position in a Person's Brain", each of which are incorporated herein in its entirety.

Once electrical stimulation lead 14 has been inserted and secured, connecting portion 16 of lead 14 extends from the lead insertion site to the implant site at which stimulation source 12 is implanted. The implant site is typically a subcutaneous pocket formed to receive and house stimulation source 12. The implant site is usually positioned a distance away from the insertion site, such as near the chest, below the clavicle or alternatively near the buttocks or another place in the torso area. Once all appropriate components of stimulation system are implanted, these components may be subject to mechanical forces and movement in response to movement of the person's body. A doctor, the patient, or another user of stimulation source may directly or indirectly input signal parameters for controlling the nature of the electrical stimulation provided.

Although example steps are illustrated and described, the present application contemplates two or more steps taking place substantially simultaneously or in a different order. In addition, the present application contemplates using methods with additional steps, fewer steps, or different steps, so long as the steps remain appropriate for implanting an example stimulation system into a person for electrical stimulation of the person's brain.

IV. INFUSION PUMPS

In further embodiments, it may be desirable to use a drug delivery system independent of or in combination with electrical stimulation of the brain. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, without being bound to a specific procedure, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Any suitable type of infusion pump can be used to deliver an appropriate therapeutic agent. For example, "active pumping" devices or so-called peristaltic pumps are described in U.S. Pat. Nos. 4,692,147, 5,840,069, and 6,036,459, which are incorporated herein by reference in their entirety. Peristaltic pumps are used to provide a metered amount of a drug in response to an electronic pulse generated by control circuitry associated within the device. An example of a commercially available peristaltic pump is SynchroMed® implantable pump from Medtronic, Inc., Minneapolis, Minn.

Other pumps that may be used include accumulator-type pumps, for example certain external infusion pumps from Minimed, Inc., Northridge, Calif. and Infusaid® implantable pump from Strato/Infusaid, Inc., Norwood, Mass. Passive pumping mechanisms can be used to release an agent in a constant flow or intermittently or in a bolus release. Passive type pumps include, for example, but are not limited to gas-driven pumps described in U.S. Pat. Nos. 3,731,681 and 3,951,147; and drive-spring diaphragm pumps described in U.S. Pat. Nos. 4,772,263, 6,666,845, 6,620,151 which are incorporated by reference in its entirety. Pumps of this type are commercially available, for example, Model 3000® from Arrow International, Reading, Pa. and IsoMed® from Medtronic, Inc., Minneapolis, Minn.; AccuRx® pump from Advanced Neuromodulation Systems, Inc., Plano, Tex.

Instances in which chemical and electrical stimulation will be administered to the subject, a catheter having electrical leads may be used, similar to the ones described in U.S. Pat. Nos. 6,176,242; 5,423,877; 5,458,631 and 5,119,832, each of which are incorporated herein by reference in its entirety.

V. IDENTIFYING A SUBJECT WITH AN AFFECTIVE DISORDER

Subjects can be selected, identified and/or diagnosed based upon the accumulation of physical, chemical, and historical behavioral data on each patient. One of skill in the art is able to perform the appropriate examinations to accumulate such data. One type of examination can include neurological examinations, which can include mental status evaluations, which can further include a psychiatric assessment. Other types of examinations can include, but are not limited to, motor examination, cranial nerve examination, and neuropsychological tests (i.e., Minnesota Multiphasic Personality Inventory, Beck Depression Inventory, or Hamilton Rating Scale for Depression).

In addition to the above examinations, imaging techniques can be used to determine normal and abnormal brain function that can result in disorders. Functional brain imaging allows for localization of specific normal and abnormal functioning of the nervous system. This includes electrical methods such as electroencephalography (EEG), magnetoencephalography (MEG), single photon emission computed tomography (SPECT), as well as metabolic and blood flow studies such as functional magnetic resonance imaging (fMRI), and positron emission tomography (PET) which can be utilized to localize brain function and dysfunction.

VI. TREATMENT OF AN AFFECTIVE DISORDER

Initially, there is an impetus to treat psychiatric disorders with direct modulation of activity in that portion of the brain causing the pathological behavior. In this regard, there have been a large number of anatomical studies that have helped to identify the neural structures and their precise connections which are implicated in psychiatric activity/disorders. These are the structures that are functioning abnormally and manifesting in psychiatric/behavioral/addiction disorders. Numerous anatomical studies from autopsies, animal studies, and imaging such as computerized tomography (CT) scans, and magnetic resonance imaging (MRI) scans have demonstrated the role of these structures and their connections in psychiatric activity/disorders. In addition to these anatomical studies, a number of physiological techniques and diagnostic tools are used to determine the physiological aberrations underlying these disorders. This includes electrical methods such as electroencephalography (EEG), magnetoencephalography (MEG), as well as metabolic and blood flow studies such as functional magnetic resonance imaging (fMRI), and positron emission tomography (PET). The combination of the anatomical and physiological studies have provided increased insight into our understanding of the structures which are involved in the normal functioning or activity of the brain and the abnormal functioning manifesting in psychiatric, behavioral and addiction disorders.

Accordingly, the present application relates to modulation of neuronal activity to affect psychological or psychiatric activity and/or mental activity. The present application finds particular application in the modulation of neuronal function or processing to effect a functional outcome. The modulation of neuronal function is particularly useful with regard to the prevention, treatment, or amelioration of psychiatric, psychological, conscious state, behavioral, mood, and thought activity (unless otherwise indicated these will be collectively referred to herein as "psychological activity" or "psychiatric activity" or "mental activity"). When referring to a pathological or undesirable condition associated with the activity, reference may be made to "psychiatric disorder" or "psychological disorder" instead of psychiatric or psychological activity. Although the activity to be modulated usually manifests itself in the form of a disorder such as a mood disorder (i.e., major depressive disorder, bipolar disorder, and dysthymic disorder) or an anxiety disorder (i.e., panic disorder, posttraumatic stress disorder, obsessive-compulsive disorder and phobic disorder), it is to be appreciated that some representative embodiments may also find application in conjunction with enhancing or diminishing any neurological or psychiatric function, not just an abnormality or disorder. Psychiatric activity that may be modulated can include, but not be limited to, normal functions such as alertness, conscious state, drive, fear, anger, anxiety, euphoria, sadness, and the fight or flight response.

The present application finds particular utility in its application to human psychological or psychiatric activity/disorder. However, it is also to be appreciated that the present application is applicable to other animals which exhibit behavior that is modulated by the brain. This may include, for example, rodents, primates, canines, felines, elephants, dolphins, etc. Utilizing some embodiments, one skilled in the art may be able to modulate the functional outcome of the brain to achieve a desirable result.

One technique that offers the ability to affect neuronal function is the delivery of electrical, chemical, and/or magnetic stimulation for neuromodulation directly to target tissues via an implanted device having a probe. The probe can be a stimulation lead or electrode assembly or drug-delivery catheter, or any combination thereof. The electrode assembly may be one electrode, multiple electrodes, or an array of electrodes in or around the target area. The proximal end of the probe can be coupled to a device, such as an electrical signal source, pharmaceutical delivery pump, or both which, in turn, is operated to stimulate the predetermined treatment site. In certain embodiments, the probe can be incorporated into the device such that the probe and the signal generating device are a single unit.

Certain embodiments involve a method of treating a mood and/or anxiety disorder comprising the steps of: surgically implanting an electrical stimulation lead having a proximal end and a stimulation portion, wherein after implantation the stimulation portion is in communication with a predetermined site; coupling the proximal end of the lead to a signal generator; and generating an electrical signal with the signal generator to modulate the predetermined site thereby treating the mood and/or anxiety disorder.

In further embodiments, neuromodulation of the predetermined site can be achieved using magnetic stimulation. One such system that can be employed and that is well known in the art is described in U.S. Pat. No. 6,425,852, which is incorporated herein by reference in its entirety.

The therapeutic system or deep brain stimulation system is surgically implanted as described in the above sections. One of skill in the art is cognizant that a variety of electrodes or electrical stimulation leads may be utilized. It is desirable to use an electrode or lead that contacts or conforms to the target site for optimal delivery of electrical stimulation. One such example, is a single multi contact electrode with eight contacts separated by 2½ mm each contract would have a span of approximately 2 mm. Another example is an electrode with two 1 cm contacts with a 2 mm intervening gap. Yet further, another example of an electrode that can be used is a 2 or 3 branched electrode/catheter to cover the predetermined site or target site. Each one of these three pronged catheters/electrodes have four contacts 1-2 mm contacts with a center to center separation of 2 of 2.5 mm and a span of 1.5 mm. Similar designs with catheters to infuse drugs with single outlet pore at the extremities of these types of catheters or along their shaft may also be designed and used.

Still further, the present application extends to methods of transplanting cells into a predetermined site to treat mood and/or anxiety disorders. It is envisioned that the transplanted cells can replace damaged, degenerating or dead neuronal cells, deliver a biologically active molecule to the predetermined site or to ameliorate a condition and/or to enhance or stimulate existing neuronal cells. Such transplantation methods are described in U.S. Application No. US20040092010, which is incorporated herein by reference in its entirety.

Cells that can be transplanted can be obtained from stem cell lines (i.e., embryonic stem cells, non-embryonic stem cells, etc.) and/or brain biopsies, including tumor biopsies, autopsies and from animal donors. (See U.S. Application No. US20040092010; U.S. Pat. Nos. 5,735,505 and 6,251,669; Temple, *Nature Reviews* 2:513-520 (2000); Bjorklund and Lindvall, *Nat. Neurosci.* 3:537-544 (2000)), each of which is incorporated herein by reference in its entirety). Brain stem cells can then be isolated (concentrated) from non-stem cells based on specific "marker" proteins present on their surface. In one such embodiment, a fluorescent antibody specific for such a marker can be used to isolate the stem cells using fluorescent cell sorting (FACS). In another embodiment an antibody affinity column can be employed. Alternatively, distinctive morphological characteristics can be employed.

The predetermined site or target area is a subcallosal area, more preferably, the subgenual cingulate area, and more preferably Brodmann area 25/Brodmann area 24. Stimulation of a subcallosal area (i.e., subgenual cingulate area or Brodmann area 25/Brodmann area 24) and/or the surrounding or adjacent white matter tracts leading to or from the subcallosal area or white matter tracts that are contiguous with the subcallosal area results in changes that alleviate or improve the mood and/or anxiety disorder of the subject. It is contemplated that modulating a subcallosal area, more particularly a subgenual cingulate area, can result in increasing, decreasing, masking, altering, overriding or restoring neuronal activity resulting in treatment of the mood and/or anxiety disorder. Yet further stimulation of a subgenual cingulate area, more particularly Brodmann area 25, results in modulation of neuronal activity of other areas of the brain, for example, Brodmann area 9, Brodmann area 10, Brodmann area 24, the hypothalamus, and the brain stem.

Using the therapeutic stimulation system, the predetermined site or target area is stimulated in an effective amount or effective treatment regimen to decrease, reduce, modulate or abrogate the mood and/or anxiety disorder. Thus, a subject is administered a therapeutically effective stimulation so that the subject has an improvement in the parameters relating to the affective disorder including subjective measures such as, for example, neurological examinations and neuropsychological tests (i.e., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS, CGI, N-BAC, or Yale-Brown Obsessive Compulsive score (Y-BOCS)), motor examination, and cranial nerve examination, and objective measures including use of additional psychiatric medications, such as anti-depressants, or other alterations in cerebral blood flow or metabolism and/or neurochemistry. The improvement is any observable or measurable improvement. Thus, one of skill in the art realizes that a treatment may improve the patient condition, but may not be a complete cure of the disease.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

According to one embodiment, the target site is stimulated using stimulation parameters such as, pulse width of about 1 to about 500 microseconds, more preferable, about 1 to about 90 microseconds; frequency of about 1 to about 300 Hz, more preferably, about 100 to about 185 Hz; and voltage of about 0.5 to about 10 volts, more preferably about 1 to about 10 volts. It is known in the art that the range for the stimulation parameters may be greater or smaller depending on the particular patient needs and can be determined by the physician. Other parameters that can be considered may include the type of stimulation for example, but not limited to acute stimulation, subacute stimulation, and/or chronic stimulation.

It is envisioned that stimulation of a subcallosal area and/or the adjacent white matter modulates other targets in the limbic-cortical circuit or pathway thereby improving any dysfunctional limbic-cortical circuits resulting in an improvement or alleviation or providing remission of depression and/or anxiety in the treated subjects. Other such improvements can be sensations of calm, tranquility, peacefulness, increased energy and alertness, improved mood, improvement in attention and thinking, improvement in motor speed, improvement in mental speed and in spontaneity of speech, improved sleep, improved appetite, improved limbic behavior, increased motivation, decreases in anxiety, decreases in repetitive behavior, impulses, obsessions, etc.

For purposes of this application, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether objective or subjective.

Figure 4:
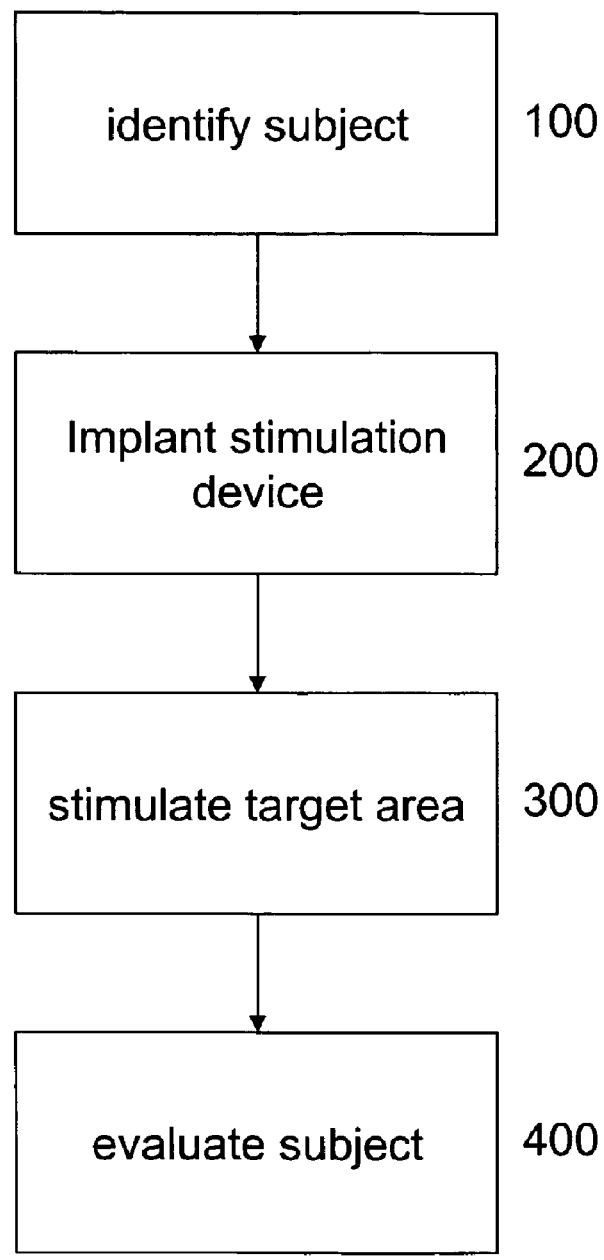
FIG. 4 is a flowchart describing the general procedure.

FIG. 4 summarizes the general procedure according to one representative embodiment. Any of the above described methods can be used to identify a subject or diagnose a subject that suffers from an affective disorder (100). Once the subject is identified, a stimulation device is implanted (200) into the subject such that the subcallosal area of the subject's brain is stimulated (300). After the target area has been stimulated (i.e., electrical, chemical or magnetic stimulation), the subject is evaluated to determine the change in the affective disorder. One of skill in the art realizes that the present application is not bound by the described methods or devices and that any method or device that would result in neuromodulation of the subcallosal area could be used.

VII. COMBINATION TREATMENT

In order to increase the effectiveness of the electrical stimulation method, it may be desirable to combine electrical stimulation with chemical stimulation to treat the mood and/or anxiety disease.

In one preferred alternative, an implantable signal generator and electrical stimulating lead and an implantable pump and catheter(s) are used to deliver electrical stimulation and/or one or more stimulating drugs to the above mentioned areas as a treatment for mood and/or anxiety disorders.

Herein, stimulating drugs comprise medications, anesthetic agents, synthetic or natural peptides or hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

Similarly, excitatory neurotransmitter agonists (i.e., norepinephrine, epinephrine, glutamate, acetylcholine, serotonin, dopamine), agonists thereof, and agents that act to increase levels of an excitatory neurotransmitter(s) (i.e., edrophonium; Mestinon; trazodone; SSRIs (i.e., flouxetine, paroxetine, sertraline, citalopram and fluvoxamine); tricyclic antidepressants (i.e., imipramine, amitriptyline, doxepin, desipramine, trimipramine and nortriptyline), monoamine oxidase inhibitors (i.e., phenelzine, tranylcypromine, isocarboxasid)), generally have an excitatory effect on neural tissue, while inhibitory neurotransmitters (i.e., dopamine, glycine, and gamma-aminobutyric acid (GABA)), agonists thereof, and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (i.e., bicuculline) and agents that act to decrease levels of an inhibitory neurotransmitter(s) have been demonstrated to excite neural tissue, leading to increased neural activity. Similarly, excitatory neurotransmitter antagonists (i.e., prazosin, and metoprolol) and agents that decrease levels of excitatory neurotransmitters may inhibit neural activity. Yet further, lithium salts and anesthetics (i.e., lidocane) may also be used in combination with electrical stimulation.

VIII. EXAMPLES

The following examples are included to demonstrate preferred embodiments, more particularly methods and procedures, according to some embodiments. It should be appreciated by those of skill in the art that the techniques disclosed in the examples which follow represent techniques discovered by the inventor to function well in the practice of some embodiments of the invention, and thus can be considered to constitute preferred modes of practice. However, those of skill in the art should, in light of the present disclosure, appreciate that many changes can be made in the specific embodiments which are disclosed and still obtain a like or similar result without departing from the spirit and scope of the appended claims.

Example 1

Patient Selection

Five patients were selected for electrical stimulation of the brain. Patients were selected based upon various demographics, family history of depression (FHx), age of onset, episodes of depression per year, the medications, other therapies, and the Hamilton rating score, as shown in Table 1. (Note "Dur yr" means duration in years).

As is known in the art, a score above 7 on the Hamilton 17 scale ("H17") is an indication of depression. A 50% change in the H17 scale score of from the initial baseline score is considered a clinical response, while a score of less than 7 is considered clinical remission.

TABLE 1

| | | | | | | | | | | | | |
|---|---|---|---|---|---|---|---|---|---|---|---|---|
| Patient Demographic | | | | | | | | | | | | |
| PT | Sex | Age | FHx | Age onset | Dur Yr | Epi yr | Meds | ECT | CBT | IPT | H17 | dx |
| A | F | 48 | Y | 18 | 20 | 2.5 | 1, 2, 4 | N | N | Y | 29 | UP |
| B | F | 45 | Y | 21 | 24 | 6 | 1, 2, 3, 5 | Y | Y | Y | 27 | UP |
| C | M | 37 | Y | 20 | 17 | 10 | 1, 2 | Y | Y | Y | 26 | UP |

TABLE 1-continued

Patient Demographic

| PT | Sex | Age | FHx | Age onset | Dur Yr | Epi yr | Meds | ECT | CBT | IPT | H17 | dx |
|---|---|---|---|---|---|---|---|---|---|---|---|---|
| D | M | 48 | Y | 36 | 12 | 5 | 1, 2, 5 | Y | Y | Y | 24 | UP |
| E | M | 59 | N | 45 | 15 | 3 | 1, 2, 3 | Y | N | Y | 20 | BPII |
|   |   | Mean 47 |   | 28 | 18 | 5 |   |   |   |   | 25 |   |

Meds: 1 = SSRI, 2 = bupropion, 3 = atypical antipsychotics, 4 = stimulates, 5 = other (benzo, and anticonvulsants).

Example 2

Surgical Procedure

Under local anesthesia, a stereotactic frame was first placed on the patient's head, followed by acquisition of an MRI (Magnetic Resonance Imaging) scan to localize the target region. Patients were then taken to the operating room where, under local anesthesia, two burr holes were placed behind the hairline. Stereotactic coordinates were derived from the pre-op MRI. The coordinates of this target derived from the Schaltenbrand and Wahren Atlas plate 3 (FIG. 3) were 6-7 mm from the midline (range 2-14 mm), 29 mm anterior to the mid-commissural point range 20-40) and 5 mm (range 0-10 mm) below the intra-commissural line.

Once the target sites were identified, two multi contact electrodes were delivered, one in each hemisphere. The electrodes were connected to a stimulating pulse generator.

With the patient's participation, each electrode contact was stimulated and acute changes in behavior was assessed using self report and mood rating scales, such as POMS, PANAS, sadness, anxiety and general well being, self-report, and mood, motor and cognitive scales, such as, finger tapping, verbal fluency. As either positive or negative changes in mood might occur, the relationship between the specific stimulation site and the resulting behavior was carefully documented. Following a testing session to help in optimal target selection and adjustment of the position of the electrode contacts, the incisions were closed and patients taken to the intensive care unit for recovery from surgery.

At anytime after the surgery for implantation of the electrodes, patients underwent a second procedure (~45 mins under general anesthesia) to connect the electrodes to a self contained subcutaneous generator device placed below the clavicle and connected to the electrodes in the head. After 2-3 days, the patients was discharged home on their regular antidepressant regime with the stimulator turned OFF.

Example 3

Outpatient Programming and Clinical Follow-up

Patients returned for generator device programming. There were several parameters that were tested, namely, which electrode contact was to be stimulated, the polarity of stimulation, the frequency and pulse width of stimulation, etc.

The electrode programming was done on an outpatient basis and involved a series of trials over the course of a week. Electrode contacts that produced acute behavioral changes or fMRI signal changes in the subgenual cingulate area (Brodmann area 25) were tried first. Once basic parameters were set, adjustments were made periodically until a stable program was established.

Once final stimulation parameters were established, psychiatric symptoms were monitored on a monthly basis. Clinical ratings were quantified using Beck, Hamilton, CGI, and Quality of Life Scales and Serial Neuropsychological Testing. Serial Neuropsychological Testing and PET studies were performed at 8 weeks and 6 months. General cognitive performance and detailed frontal lobe functioning was assessed. The test battery was designed to differentiate dorsolateral, superior medial, and ventrolateral/orbital frontal behaviors which was differently affected by activation or disruption of the target areas with electrical stimulation. Serial testing allowed differentiation between early surgical effects, chronic stimulation effects, and correlations with mood change.

Figure 5A:
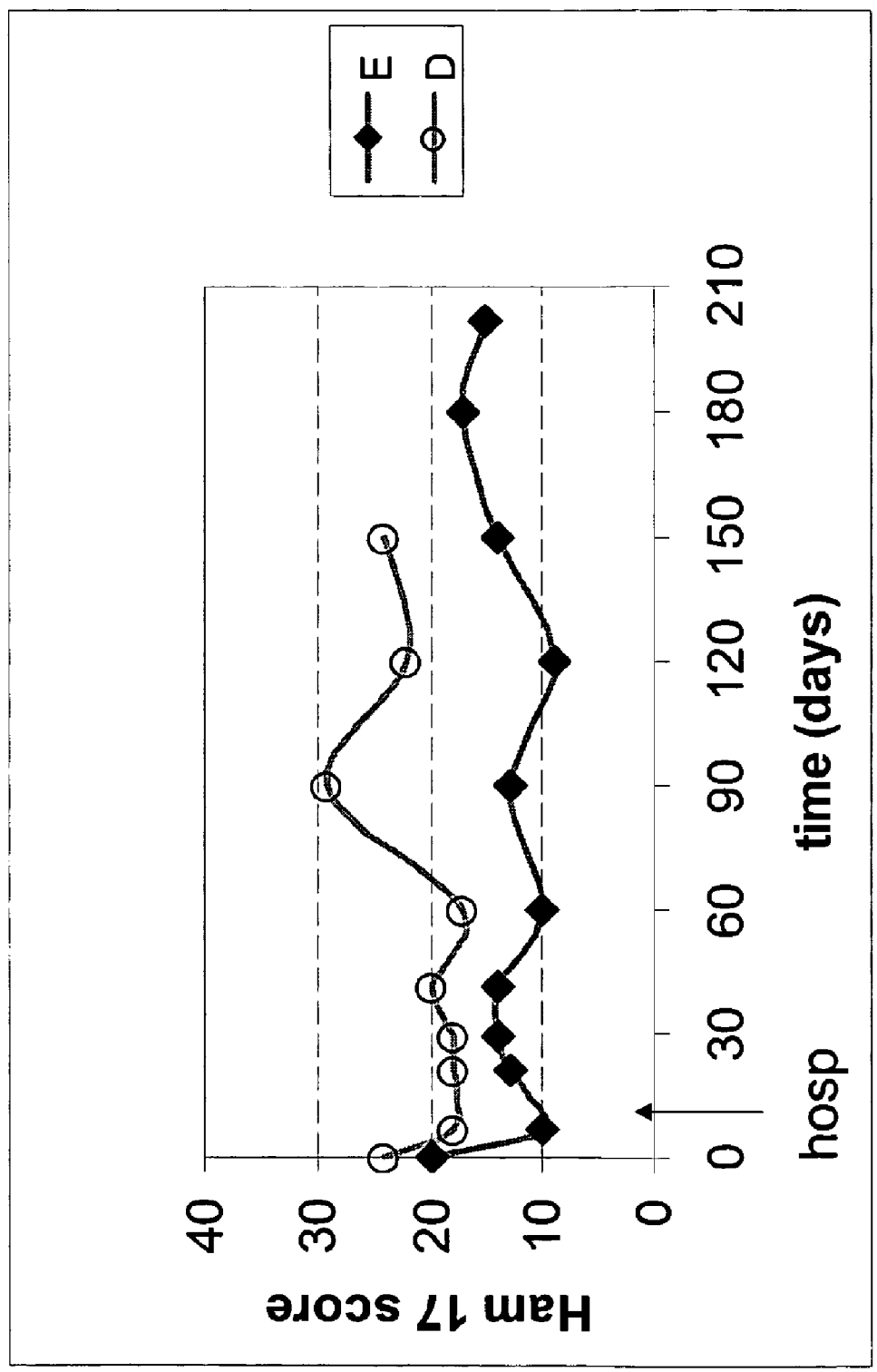
FIGS. 5A and 5B shows a graphical analysis of scores based upon the Hamilton Rating Scale for Depression after deep brain stimulation treatment.
Figure 5B:
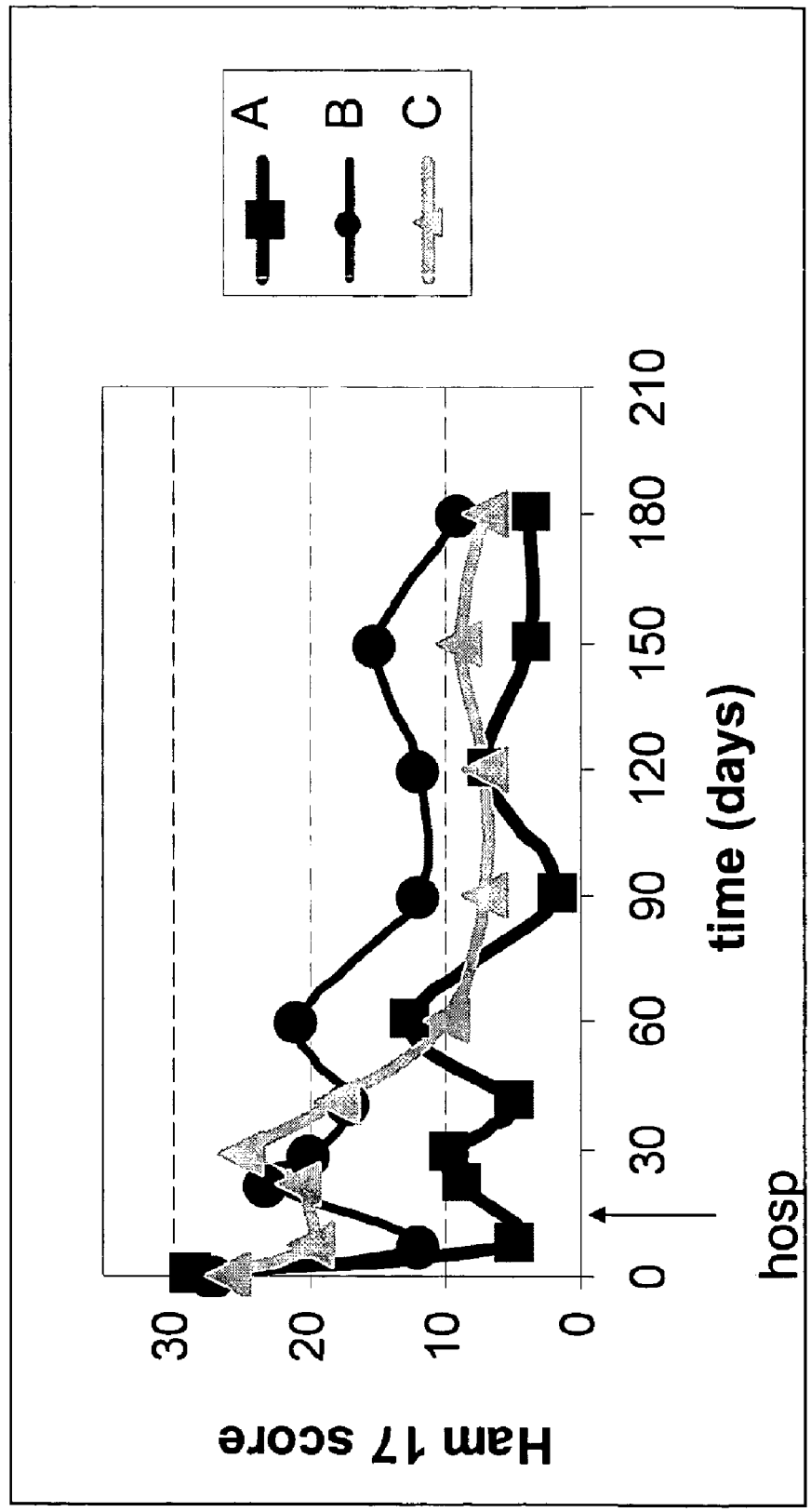
Figure 6A:
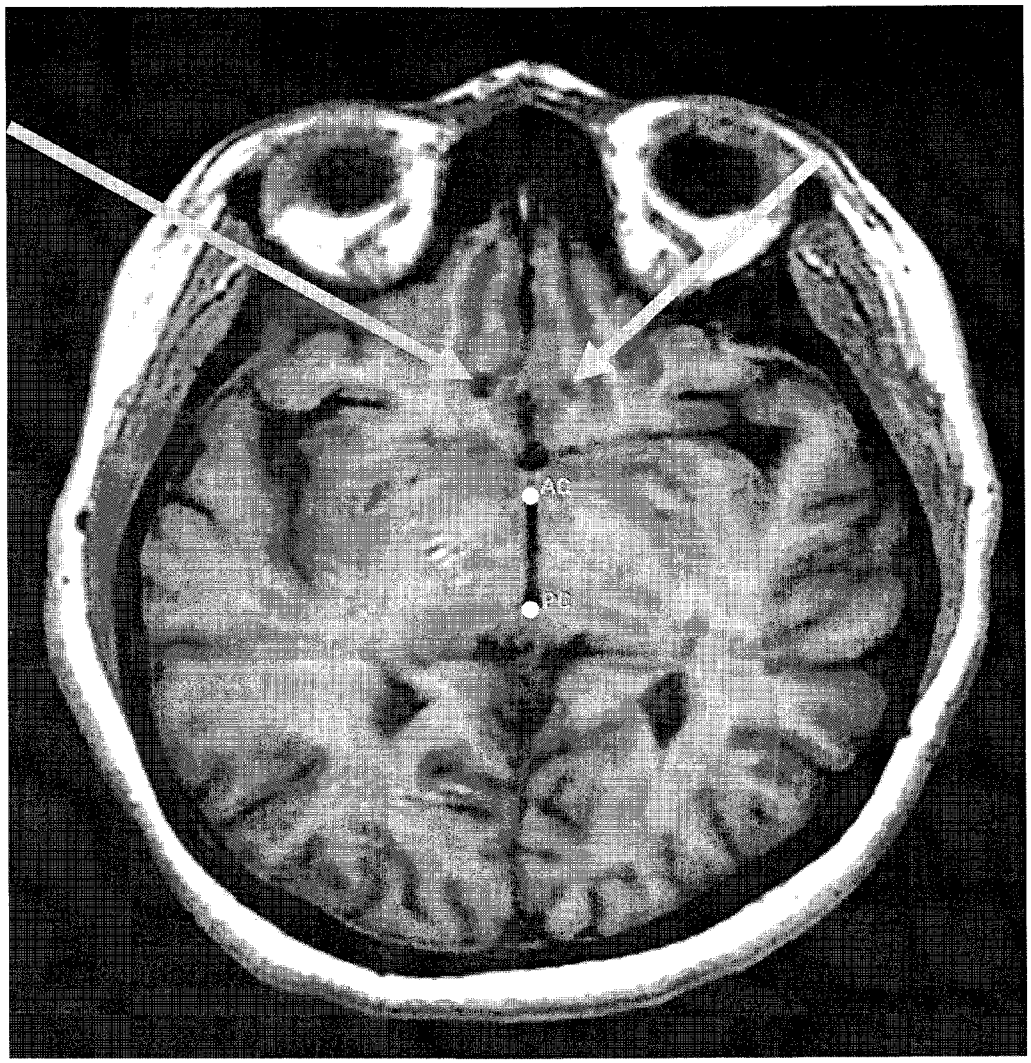
FIGS. 6A-6E show scans through various planes of the brain.
Figure 6B:
Figure 6C:
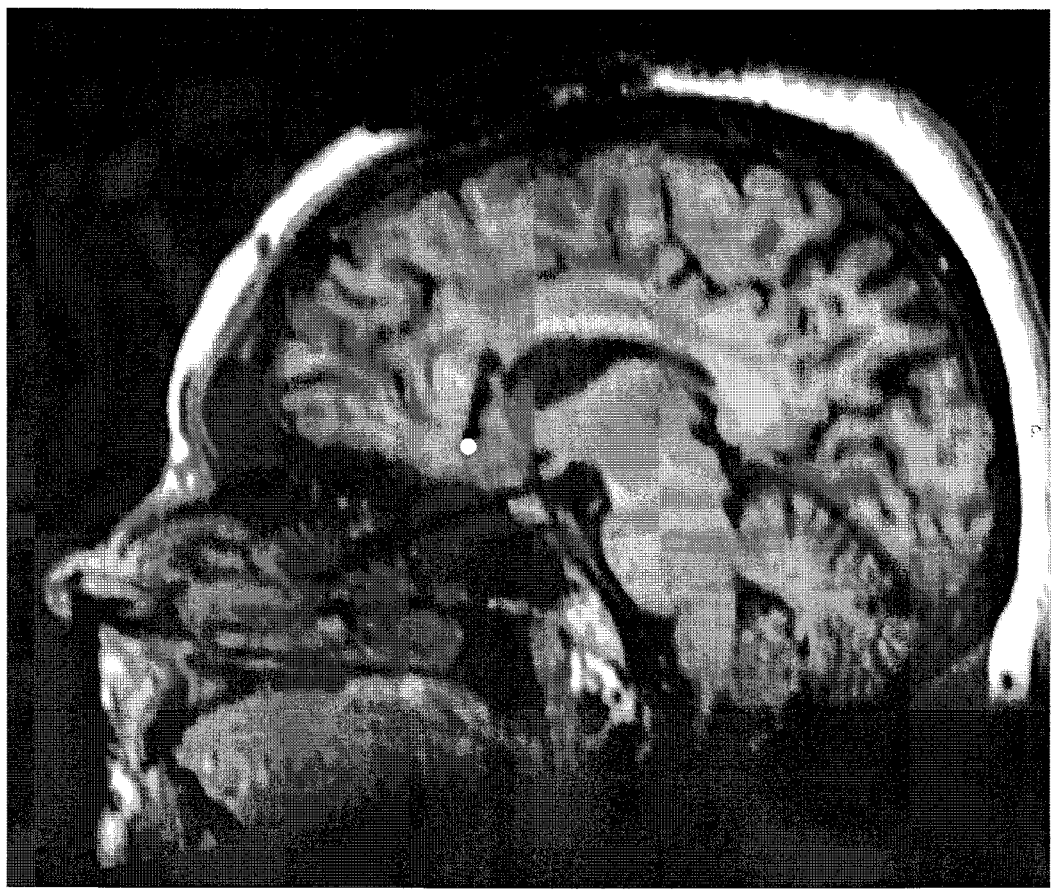
Figure 6D:
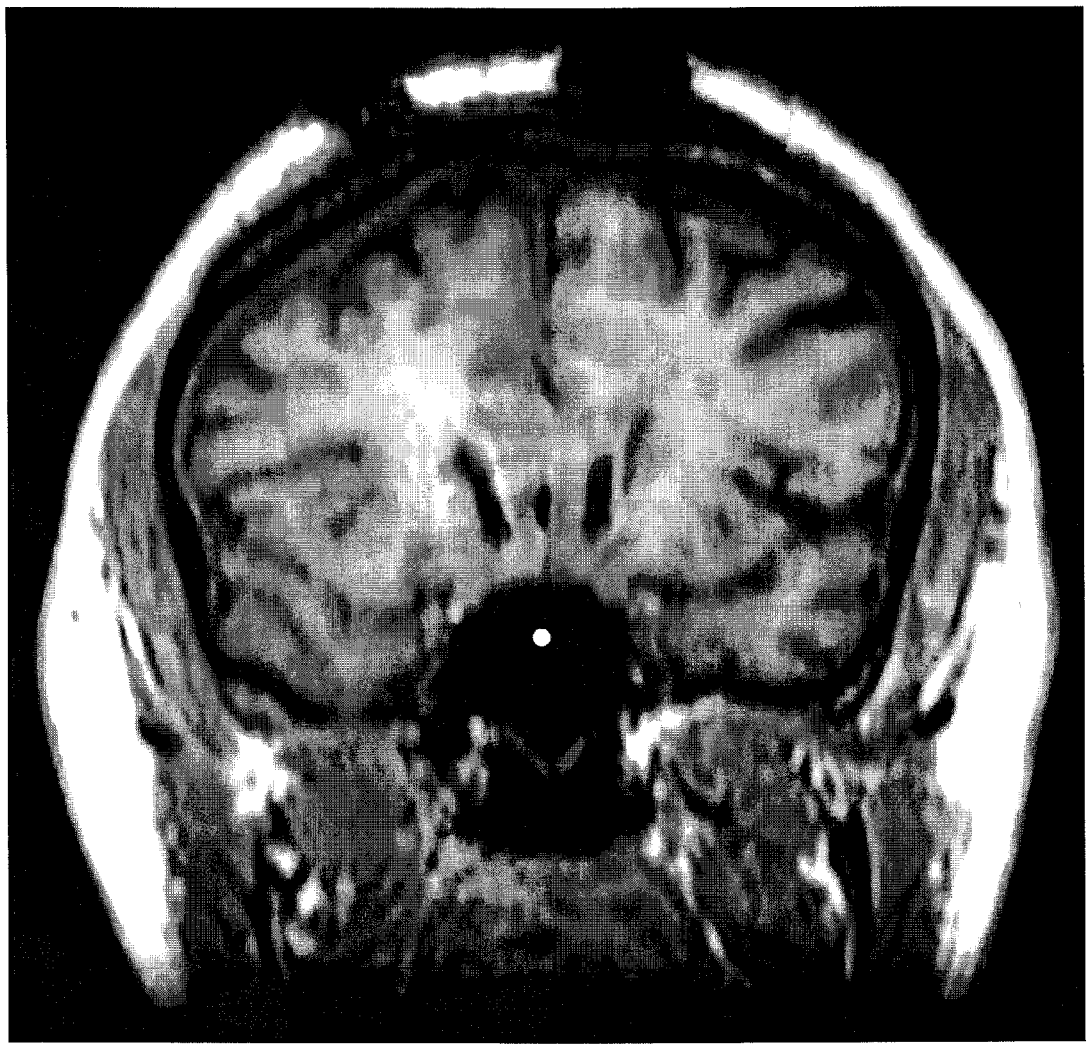
Figure 6E:

FIG. 5A and FIG. 5B show the results of the Hamilton Scale Scores after 6 months of stimulation for the first five subjects.

Thus, stimulation in a subcallosal white matter area in communication with Brodmann area 25 leads to changes in the activity of Brodmann area 25, the dorsal/lateral frontal lobe (Brodmann areas 9 and 6), dorsal/medial frontal lobe (Brodmann areas 9 and 10), anterior cingulate area (Brodmann area 24), orbital frontal cortex (Brodmann areas 10 and 11), the hypothalamus, brain stem and other target areas such as upstream, downstream or remote cortical and subcortical regions.

Example 4

Mapping Using fMRI

Within 1-5 days of the initial electrode surgery, fMRI scans were performed during successive stimulation of each electrode contact. fMRI was used as an additional means of mapping the differences in activity of the electrodes. fMRI was not required because the optimal electrode was determined based upon clinical observations during the operation and operatively, as described above.

This procedure was used to further define the differential projection fields mediating acute changes in behavior initiated by a particular stimulation site. Even without acute changes in behavior, these maps allowed discrimination of subtle differences in pathways served by stimulation of different white matter tracts within the stimulation field of each electrode. These results were also useful in guiding selection of the optimal site for chronic stimulation, particularly if changes with some but not all electrodes were seen in the target subgenual cingulate area.

Imaging was performed on a 1.5T scanner using methods proven safe for patients with implanted electrodes and delivery catheters (FIG. 6A-6E). Whole brain samples using spiral acquisition were repeated every 3.52 seconds. One cycle was 120 seconds of stimulation and 120 seconds rest. A block of 4 cycles was acquired for the best and worst contact pairs within each hemisphere based on behavior changes in the operating room and post-operatively. The electrodes were activated using a transcutaneous lead connected to a pulse generator outside the imaging room. Patients rated mood (pos/neg) on a 1-5 scale by button push and auditory prompt following each cycle. Analyses addressed differences ON vs OFF for each contact and changes over multiple cycles.

REFERENCES

All patents and publications mentioned in the specifications are indicative of the levels of those skilled in the art to which the application pertains. All patents and publications are herein incorporated by reference to the same extent as if each individual publication was specifically and individually indicated to be incorporated by reference.
Bjorklund and Lindvall, Nat. Neurosci. 3:537-544 (2000)
Drevets et al., Nature 386:824-7, 1997.
Ebmeier et al., Br J Psychiatry, 170:77-81, 1997.
Galynker et al., J Nucl Med., 39:608-12, 1998.
Temple, Nature Reviews 2:513-520 (2000)
U.S. Pat. No. 3,731,681
U.S. Pat. No. 3,951,147
U.S. Pat. No. 4,692,147
U.S. Pat. No. 4,772,263
U.S. Pat. No. 5,119,832
U.S. Pat. No. 5,263,480
U.S. Pat. No. 5,299,569
U.S. Pat. No. 5,423,877
U.S. Pat. No. 5,458,631
U.S. Pat. No. 5,470,846
U.S. Pat. No. 5,540,734
U.S. Pat. No. 5,735,505
U.S. Pat. No. 5,840,069
U.S. Pat. No. 6,016,449
U.S. Pat. No. 6,036,459
U.S. Pat. No. 6,051,017
U.S. Pat. No. 6,176,242
U.S. Pat. No. 6,251,669
U.S. Pat. No. 6,425,852
U.S. Pat. No. 6,609,031
U.S. Pat. No. 6,620,151
U.S. Pat. No. 6,666,845
U.S. Pat. No. 6,735,474
U.S. Pat. No. 6,735,475
U.S. Publication No. US20040092010

Although some embodiments and advantages have been described in detail, it should be understood that various changes, substitutions and alterations can be made herein without departing from the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

We claim:

1. A method of treating a mood or anxiety disorder in a patient comprising:
    implanting a stimulation lead within the patient such that at least one electrode of the lead is positioned in or in direct contact with neural tissue of the gray and white matter inferior to the corpus callosum and posterior to the anterior most portion of the genu of the corpus callosum;
    coupling the lead to a pulse generator;
    generating electrical pulses using a pulse generator;
    conducting the electrical pulses from the pulse generator through a stimulation lead; and
    applying the electrical pulses to stimulate neural tissue of the gray and white matter inferior to the corpus callosum and posterior to the anterior most portion of the genu of the corpus callosum of the patient utilizing the at least one electrode of the stimulation lead, wherein the applying the electrical pulses effectively treats the mood or anxiety of the patient.

2. The method of claim 1, wherein the neural tissue comprises the subcallosal white matter and adjacent cortex.

3. The method of claim 2, wherein the neural tissue comprises the subcallosal white matter.

4. The method of claim 2, wherein the neural tissue includes the subgenual cingulate gyrus and surrounding white matter.

5. The method of claim 4, wherein the subgenual cingulate gyrus and surrounding white matter comprises Brodmann area 25.

6. The method of claim 5, wherein the subgenual cingulate gyrus and surrounding white matter comprises subgenual Brodmann area 24.

7. The method of claim 1 further comprising evaluating the patient to determine the effectiveness of the treatment.

8. The method of claim 7, wherein adjustments to parameters are made based upon the evaluation to increase the effectiveness of the treatment.

9. The method of claim 1, wherein after implantation the at least one electrode is positioned about 20 mm to about 40 mm anterior to the anterior commissure.

10. The method of claim 9, wherein after implantation the at least one electrode is positioned about 20 mm to about 30 mm anterior to the anterior commissure.

11. The method of claim 1, wherein the mood disorder is selected from the group consisting of major depressive disorder, and bipolar disorder.

12. The method of claim 1, wherein the anxiety disorder is selected from the group consisting of panic disorder, post-traumatic stress disorder, obsessive-compulsive disorder and phobic disorder.

13. The method of claim 1, wherein the mood disorder is major depressive disorder.

14. The method of claim 13, wherein the treatment for the major depressive disorder of the patient results in partial or complete remission of the disorder.

15. The method of claim 1, wherein the generating, conducting, and applying are performed on a chronic basis.

16. A method of treating depression, mood disorder and/or anxiety disorder in a patient comprising:
    implanting a stimulation lead within the patient such that at least one electrode of the lead is positioned in or in direct contact with neural tissue of the gray and white matter inferior to the rostrum and genu of the corpus callosum and about 20 to about 40 mm anterior to the anterior commissure;
    coupling the lead to a pulse generator;
    generating electrical pulses using a pulse generator;
    conducting the electrical pulses from the pulse generator through a stimulation lead; and
    applying the electrical pulses to stimulate neural tissue of the medial gray and white matter inferior to the rostrum and genu of the corpus callosum and about 20 to about 40 mm anterior to the anterior commissure of the patient utilizing the at least one electrode of the stimulation lead, wherein the applying the electrical pulses effectively treats the depression, mood disorder and/or anxiety disorder of the patient.

17. The method of claim 16, wherein after implantation the at least one electrode is positioned about 20 mm to about 30 mm anterior to the anterior commissure.

18. The method of claim 16, wherein the neural tissue comprises the subcallosal white matter and adjacent cortex.

19. The method of claim 18, wherein the subcallosal white matter and adjacent cortex comprises Brodmann area 25.

20. The method of claim 18, wherein the at least one electrode is implanted within the subcallosal white matter.

21. The method of claim 19, wherein the at least one electrode is implanted within a white matter tract contiguous with Brodmann area 25.

22. A method of treating depression, mood disorder or anxiety disorder in a patient, comprising:
   implanting a stimulation lead within the patient such that at least one electrode of the lead is positioned in neural tissue about 0 mm to 10 mm below the intra-commissural line, about 2 mm to 14 mm from midline and about 20 to about 40 mm anterior to the anterior commissure;
   coupling the lead to a pulse generator;
   generating electrical pulses using the pulse generator;
   conducting the electrical pulses from the pulse generator through the stimulation lead; and
   applying the electrical pulses to stimulate the neural tissue of the patient utilizing the at least one electrode of the stimulation lead, wherein the applying the electrical pulses effectively treats the depression, mood disorder or anxiety disorder of the patient.

23. The method of claim 22, wherein after implantation the at least one electrode is positioned about 20 mm to about 30 mm anterior to the anterior commissure.

24. The method of claim 22 further comprising identifying an approximate location to position the stimulation lead in the patient by utilizing an imaging system.

25. The method of claim 22, wherein the neural tissue comprises the gray and white matter of the subcallosal area that is inferior to the rostrum and genu of the corpus callosum including Brodmann area 25 and subgenual Brodmann area 24.

26. A method of treating depression, mood disorder or anxiety disorders in a patient, comprising:
   implanting a stimulation lead within the patient such that at least one electrode of the lead is positioned in direct contact with or directly in the subcallosal gyrus area including the surrounding white matter;
   generating electrical pulses using an implantable pulse generator (IPG) that is implanted within the patient;
   conducting the electrical pulses from the IPG through a stimulation lead; and
   applying the electrical pulses to stimulate neural tissue of the subcallosal gyrus area including the surrounding white matter of the patient utilizing the at least one electrode of the stimulation lead, wherein the applying the electrical pulses effectively treats the depression, mood disorder and/or anxiety disorder of the patient.

27. The method of claim 26, wherein treating the patient's depression, mood disorder and/or anxiety disorder improves the patient's appetite.

28. A method of improving a patient's appetite, comprising:
   implanting a stimulation lead within the patient such that at least one electrode of the lead is positioned in direct contact with or directly in the subcallosal gyrus area including the surrounding white matter;
   generating electrical pulses using an implantable pulse generator (IPG) that is implanted within the patient;
   conducting the electrical pulses from the IPG through a stimulation lead; and
   applying the electrical pulses to stimulate neural tissue of the subcallosal gyrus area including the surrounding white matter of the patient utilizing the at least one electrode of the stimulation lead, wherein the applying the electrical pulses effectively improves the patient's appetite.

* * * * *

UNITED STATES PATENT AND TRADEMARK OFFICE
CERTIFICATE OF CORRECTION

PATENT NO. : 7,653,433 B2
APPLICATION NO. : 11/469669
DATED : January 26, 2010
INVENTOR(S) : Lozano et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 448 days.

Signed and Sealed this

Twenty-third Day of November, 2010

David J. Kappos
*Director of the United States Patent and Trademark Office*